US006544744B1

(12) United States Patent
Mathies et al.

(10) Patent No.: US 6,544,744 B1
(45) Date of Patent: *Apr. 8, 2003

(54) PROBES LABELED WITH ENERGY TRANSFER COUPLED DYES

(75) Inventors: Richard Mathies, Moraga, CA (US); Alexander Glazer, Orinda, CA (US); Jingyue Ju, Redwood City, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/819,050

(22) Filed: Jan. 20, 2000

Related U.S. Application Data

(63) Continuation of application No. 08/646,861, filed on May 8, 1996, now Pat. No. 6,028,190, which is a continuation-in-part of application No. 08/411,573, filed on Mar. 27, 1995, now abandoned, and a continuation-in-part of application No. 08/410,808, filed on Mar. 27, 1995, now Pat. No. 5,707,804, which is a continuation-in-part of application No. 08/189,924, filed on Feb. 1, 1994, now Pat. No. 5,654,419.

(51) Int. Cl.[7] .............. C12Q 1/68; C12P 19/34; C07H 21/02; C07H 21/04
(52) U.S. Cl. .............. 435/6; 435/91.1; 435/91.2; 536/23.1; 536/24.3
(58) Field of Search .............. 435/6, 91.1, 91.2; 536/23.1, 24.3

(56) References Cited

U.S. PATENT DOCUMENTS

| | | |
|---|---|---|
| 4,289,750 A | 9/1981 | Kopp et al. |
| 4,451,454 A | 5/1984 | Wong |
| 4,496,553 A | 1/1985 | Halskov |

(List continued on next page.)

FOREIGN PATENT DOCUMENTS

| | | |
|---|---|---|
| EP | 86116652.3 | 12/1986 |
| EP | 0 343 993 A1 | 11/1989 |
| EP | 0 381 414 A2 | 8/1990 |
| EP | 0 381 414 A3 | 8/1990 |
| EP | 0229943 | 9/1991 |
| EP | 601889 | 6/1994 |
| GB | 2301833 | 12/1996 |
| JP | S61-44353 | 3/1986 |
| JP | 5-60698 | 9/1991 |
| JP | 05-060698 A | 3/1993 |
| WO | 84/03285 | 8/1984 |
| WO | 89/03041 | 4/1989 |
| WO | WO 90/03446 | 4/1990 |
| WO | WO 91/04018 | 4/1991 |
| WO | 92/00388 | 1/1992 |
| WO | WO 92/09270 | 6/1992 |
| WO | 92/14845 | 9/1992 |
| WO | WO 93/06482 | 4/1993 |
| WO | 93/09128 | 5/1993 |
| WO | WO 93/10267 | 5/1993 |
| WO | 93/92128 | 5/1993 |
| WO | 93/23492 | 11/1993 |
| WO | 94/06812 | 3/1994 |
| WO | 94/17397 | 8/1994 |
| WO | 94/28166 | 12/1994 |
| WO | 96/04405 | 2/1996 |
| WO | 96/41166 | 12/1996 |

OTHER PUBLICATIONS

Abdel–Mottaleb, M. S. A., et al., "Photophysics and dynamics of coumarin laser dyes and their analytical implications" Proc..–Indian Acad. Sci. Chem. Sci. 1992, 104, 185–195.

Ansorge, W., Sproat, B., Stegemann, J., Schwager, C., Zenke, M., "Automated DNA sequencing: ultrasensitive detection of fluorescent bands during electrophoresis," *Nucleic Acids Research*, vol. 15, No. 11, pp. 4593–4602, 1987.

Anton, J.A., et al., "Transfer of excitation energy between porphyrin centers of a covalently linked dimer." Photochem. Photobiol. 1978, 28, 235–242.

Benson, S. C., et al., "Fluorescence energy–transfer cyanine heterodimers with high affinity for double–stranded DNA. I. Synthesis and spectroscopic properties." Anal. Biochem. 1995, 231, 247–255.

Bothner–By, A.A., Dadok, J., Johnson, T.E., Lindsey, J.S., "Molecular Dynamics of Covalently–Linked Multi–Porphyrin Arrays," J. Phys. Chem., vol. 100 (1996), pp. 17551–17557.

Butler, J.M., McCord, B.R., Jung, J.M., Allen, R.O.,, "Rapid Analysis of the Short Tandem Repeat HUMTH01 by Capillary Electrophoresis," *BioTechniques*, vol. 17, No. 6, pp. 1062–1070, 1994.

Chiu, H.C., Bersohn, R., "Electronic energy transfer between tyrosine and tryptophan in the peptides Tyr–(Pro)n–Tyr," Biopolymers (1977), 16, 277.

Clark, S.M., Mathies, R.A., "High–Speed Parallel Separation of DNA Restriction Fragments Using Capillary Array Electophoresis[1]," *Analytical Biochemistry*, 215, 163–170, 1993.

Clegg, Murchie, Zechel, Carlberg, Diekmann, Lilley, "Fluorescence Resonance Energy Transfer Analysis of the Structure of the Four–Way DNA Junction," *Biochemistry*, 31:4846–56, 1992.

(List continued on next page.)

*Primary Examiner*—W. Gary Jones
*Assistant Examiner*—Arun Chakrabarti
(74) *Attorney, Agent, or Firm*—Townsend and Townsend and Crew, LLP

(57) ABSTRACT

Fluorescent labels having at least one donor and at least one acceptor fluorophore bonded to a polymeric backbone in energy transfer relationship, as well as methods for their use, are provided. Of particular interest are the subject labels wherein the polymeric backbone is a nucleic acid and the donor fluorophore is bonded to the 5' terminus of said nucleic acid. Such labels find use as primers in applications involving nucleic acid chain extension, such as sequencing, PCR and the like.

30 Claims, 17 Drawing Sheets

U.S. PATENT DOCUMENTS

| | | | |
|---|---|---|---|
| 4,632,911 A | 12/1986 | Bauer | |
| 4,642,111 A | 2/1987 | Sakamoto et al. | |
| 4,744,987 A | 5/1988 | Mehra et al. | |
| 4,777,128 A | 10/1988 | Lippa | |
| 4,855,225 A | 8/1989 | Fung et al. | 435/6 |
| 4,868,103 A | 9/1989 | Stavrianopoulos et al. | 435/5 |
| 4,980,173 A | 12/1990 | Halskov | |
| 4,996,143 A | 2/1991 | Heller et al. | |
| 5,026,559 A | 6/1991 | Eichel et al. | |
| 5,118,802 A | 6/1992 | Smith et al. | |
| 5,188,934 A | 2/1993 | Menchen et al. | 435/6 |
| 5,210,015 A | 5/1993 | Gelfand et al. | |
| 5,217,866 A | 6/1993 | Summerton et al. | 435/6 |
| 5,254,477 A | 10/1993 | Walt | |
| 5,314,809 A | 5/1994 | Erlich et al. | |
| 5,326,692 A | 7/1994 | Brinkley et al. | |
| 5,342,789 A | 8/1994 | Chick et al. | 436/501 |
| 5,401,847 A | 3/1995 | Glazer et al. | |
| 5,410,030 A | 4/1995 | Yue et al. | |
| 5,439,797 A | 8/1995 | Tsien et al. | |
| 5,514,663 A | 5/1996 | Mandel | |
| 5,516,633 A * | 5/1996 | Fuller et al. | |
| 5,532,129 A | 7/1996 | Heller | |
| 5,552,540 A | 9/1996 | Haralambidis | |
| 5,556,964 A | 9/1996 | Hofstraat et al. | |
| 5,565,322 A | 10/1996 | Heller | |
| 5,565,554 A | 10/1996 | Glazer et al. | |
| 5,573,909 A | 11/1996 | Singer et al. | |
| 5,582,977 A | 12/1996 | Yue et al. | |
| 5,631,022 A | 5/1997 | Mandel et al. | |
| 5,646,264 A | 7/1997 | Glazer et al. | |
| 5,651,983 A | 7/1997 | Kelm et al. | |
| 5,654,419 A | 8/1997 | Mathies et al. | |
| 5,656,290 A | 8/1997 | Kelm et al. | |
| 5,670,158 A | 9/1997 | Davis et al. | |
| 5,686,105 A | 11/1997 | Kelm et al. | |
| 5,686,106 A | 11/1997 | Kelm et al. | |
| 5,688,648 A | 11/1997 | Mathies et al. | |
| 5,691,343 A | 11/1997 | Sandborn | |
| 5,707,804 A * | 1/1998 | Mathies et al. | |
| 5,728,528 A | 3/1998 | Mathies et al. | |
| 5,728,529 A | 3/1998 | Metzker et al. | 435/6 |
| 5,760,201 A | 6/1998 | Glazer et al. | |
| 5,763,189 A | 6/1998 | Beuchler et al. | |
| 5,814,336 A | 9/1998 | Kelm et al. | |
| 5,824,799 A | 10/1998 | Beuchler et al. | |
| 5,843,479 A | 12/1998 | Kelm et al. | |
| 5,843,658 A | 12/1998 | Uchiyama et al. | |
| 5,851,778 A | 12/1998 | Oh et al. | |
| 5,869,255 A | 2/1999 | Mathies et al. | 435/6 |
| 5,908,833 A | 6/1999 | Brattsand et al. | |
| 5,945,283 A | 8/1999 | Kowk et al. | |
| 5,981,200 A | 11/1999 | Tsien et al. | |
| 6,008,373 A | 12/1999 | Waggoner et al. | |
| 6,028,190 A | 2/2000 | Mathies et al. | |
| 6,048,982 A | 4/2000 | Waggoner | |
| 6,177,247 B1 | 1/2001 | Mathies et al. | |

OTHER PUBLICATIONS

Clegg, R.M., Murchie, A.I.H., Zechel, A., Lilley, D.M.J., "Observing the helical geometry of double–stranded DNA in solution by fluorescence resonance energy transfer," *Proc. Natl.Acad.Sci.*, USA, vol. 90, pp. 2994–2998, Apr., 1993, Biophysics.

Conrad, R.H., Brand, L., "Intramolecular transfer of excitation from tryptophan to 1–dimethylaminonaphthalene–5–sulfonamide in a series of model compounds." Biochemistry 1968, 7, 5777.

Delaney, J.K., Mauzerall, D.C., Lindsey, J.S., "Electron Tunneling in a Cofacial Zinc Porphyrin–Quinone Cage Molecule: Novel Temperature and Solvent Dependent," J. Am. Chem. Soc., vol. 112, No. 3 (Jan. 31, 1990), pp. 957–963.

Dirks, G., Moore, A.L., Gust, D., "Light Absorption and Energy Transfer in Polyene–Porphyrin Esters," Photochemistry and Photobiology, vol. 32 (1980), pp. 277–280.

Effenberger, F., Schlosser, H, Bäuerle, P., Maier, S., Port, H., Wolf, H.C., "Synthesis and Optical Properties of Terminally Substituted Conjugated Polyenes," Angew. Chem. Int. Ed. Engl., vol. 27, No. 2, (1988), pp. 281–284.

Florkin, M., Statz, E. H., Eds., "Mechanism of Energy Transfer" in Comprehensive Biochemistry, vol. 22, Elsevier, New York, 1967, 61.

Förster, T., "Intermolecular energy migration and fluorescence" Ann. Physik (Leipzig) 1948, 2, 55.

Fregeau and Fourney, "DNA Typing with Fluorescently Tagged Short Tandem Repeats: A Sensitive and Accurate Approach to Human Identification," *Biotechniques* 15:100–119, Jul., 1993.

Frey "Detection of Bromodeoxyuridine Incorporation by Alternation of the Fluorescence Emission from Nucleic Acid Binding Dyes Using Only an Argon Ion Laser," *Cytometry* 17:310–318, 1994.

Geyson, H.M., Mason, T.J., Rodda, S.J., "Cognitive Features of Continuous Antigenic Determinants", *Journal of Molecular Recognition*, vol. 1, No. 1, pp. 32–41, 1988.

Glazer, A.N., Stryer, L., "Fluorescent Tandem Phycobiliprotein Conjugates. Emission Wavelength Shifting by Energy Transfer" *Biophys.J.Biophysical Society*, vol. 43, pp. 383–386, Sep. 1983.

Glen Research Catalog, Glen Research Corporation, 44901 Falon Place, Sterling, Virginia 20166, 1992.

Gust, D., Moore, T.A., "A Synthetic System Mimicking the Energy Transfer and Charge Separation of Natural Photosynthesis," Journal of Photochemistry, vol. 29 (1985), pp. 173–184.

Ha, T., et al., "Probing the interaction between two single molecules: fluoresence resonance energy transfer between a single donor and a single acceptor." Proc. Nat. Acad. Sci. 1996, 93 (13) 6264–6268.

Hammond, H.A., Jin, L., Zhong, Y., Caskey, C.T., Chakraborty, R., "Evaluation of 13 Short Tandem Repeat Loci for Use in Personal Identification Applications," *Am.J.Hum.Genet.*, 55:175–189, 1994.

Haralambidis, J., Chai, M., Tregear, G.W., "Preparation of base–modified nucleosides suitable for non–radioactive label attachment and their Incorporation into synthetic oligodeoxyribonucleotides," Nucleic Acids Research, vol. 15, No. 12 (1987) pp. 4857–4876.

Hass, E., et al., "Distribution of end–to–end distances in oligopeptides in solution as estimated by energy transfer" Proc. Natl. Acad. Sci USA 1975, 72, 1807.

Haugland, R.P., et al., Dependence of the kinetics of singlet–singlet energy transfer on spectral overlap Proc. Natl. Acad. Sci. 1969, 63, 23–30.

Haugland, R.P., "Fluorescent Labels" Biosense, Fiberopt, 1991, 85–110.

Haugland, R.P., author of Molecular Probes Handbook of Fluorescent Probes and Research Chemicals (1992–1994).

Haugland, Kang, Whitaker, "New Dyes for DNA Sequencing," Molecular Probes, Inc., Eugene, OR, 97402.

Heller, Hennesey, Ruth, Jablonski "Fluorescent Energy Transfer Oligonucleotide Probes," Molecular Biosystem, Inc., San Diego, CA, 92121 ASBC Meeting, Jun. 8, 1987; *Federation Proceedings*, 46(6):1968 (1987).

Hirzel, T K., "Singlet excitation transfer between terminal chromophores in 1,4–disubstituted bicyclo (2.2.2) octanes and 4,4'–disubstituted—1,1'–dibicyclo (2.2.2) octyls" Ph.D. Dissertation, 1980, University of Wisconsin—Madison.

Hiyoshi, M., Hosoi, S., "Assay of DNA Denaturation by Polymerase Chain Reaction–Driven Fluorescent Label Incorporation and Fluorescence Resonance Energy Transfer," *Analytical Biochemistry* 221:306–311, 1994.

Holgersson,, S., Karlsson, J., Kihlgren, A., Rosén, B., Savolainen, P., Gyllensten, U., "Fluorescent–based typing of the two short tandem repeat loci HUMTH01 and HUMACTBP2: Reproducibility of size measurements and genetic variation in the swedish population," *Electrophoresis*, 15, 89–895, 1994.

Hsiao, J.S., Krueger, B.P., Wagner, R.W., Johnson, T.E., Delaney, J.K., Mauzerall, D.C., Fleming, G.R., Lindsey, J.S., Bocian, D.F., Donohoe, R.J., "Soluble Synthetic Multiporphyrin Arrays. 2. Photodynamics of Energy–Transfer Processes," *J. Am. Chem. Soc.*, vol. 118, No. 45 (Nov. 13, 1996), pp. 11181–11193.

Huang, Quesada, Mathies "DNA Sequencing Using Capillary Array Electrophoresis," *Anal. Chem.*, 64:2149–2154, 1992.

Hung, S. C., et al., "Cyanine dyes with high absorption cross section as donor chromophores in energy transfer primers" Anal. Biochem. 1996, 243, 15–27.

Hung, S.C., et al., "Energy transfer primers with 5– or 6–carboxyrhodamine–6G a acceptor chromophores" Anal. Biochem. 1996, 238, 165–170.

Hwang, K.C., Mauzerall, D., Wagner, R.W., Lindsey, J.S., "Synthesis of Amphipathic Porphyrings and Their Photoinduced Electron Transfer Reactions at the Lipid Bilayer–Water Interface," Photochemistry and Photobiology, vol. 59 (1994), pp. 145–151.

Ju, J., et al., "Cassette labeling for facile construction of energy transfer fluorescent primers" Nucleic Acid Res. 1996, 24, 1144–1148.

Ju, J., et al., "Design and synthesis of fluorescent energy transfer dye–labeled primers and their application of DNA sequencing and analysis" Anal. Biochem. 1995, 231, 131–140.

Ju, J., Ruan, C., Fuller, C., Glazer, A., Mathies, R.A., "Fluorescence energy transfer dye–labeled primers for DNA sequencing and analysis (Förster energy transfer/oligodeoxynucleotide systhesis/primer labeling/fluorescent tags)," Proc.Natl.Acad.Sci, USA, vol. 92 pp. 4347–4351, May, 1995, Biophysics.

Katz, H.E., Lavell, W.T., "4–Piperidinylimino : a nearly linear head–to–tail linking group for dipolar chromophores" J. Org. Chem. 1991, 56, 2282–2284.

Khanna, P.L., Ullman, E.F., 4'5'–Dimethoxy–6–carboxyfluorescein: A Novel Dipole–Dipole Coupled Fluorescence Energy Transfer Acceptor Useful for Fluorescence Immunoassays1, Analytical Biochemistry, 108:156–161, 1980.

Kimpton, et al., "Automated DNA Profiling Employing Multiplex Amplification of Short Tandem Repeat Loci," *PCR Methods and Applications*, 3:13–22, 1993.

Lamola, A.A., et al., "Intramolecular energy transfer between nonconjugated chromophores in some model compounds" J. Am. Chem. Soc. 1965, 37, 2322.

Latt, S. A., et al., "Energy Transfer. A system with relatively fixed Donor–Acceptor Separation" J. Am. Chem. Soc. 1965, 87, 995–1003.

Lerho, M.J., "Diffusion—enhanced fluorescence energy transfer (DEFET): Application to the study of ligands—DNA and—chromatin interaction" PhD Dissertation 1991: Universite de l'etat a Liege (Belgium).

Lindsey, J.S., Brown, P.A., Siesel, D.A., "Visible Light–Harvesting in Covalently–Linked Porphyrin–Cyanine Dyes," Tetrahedron, vol. 45, No. 15 (1989), pp. 4845–4866.

Lindsey, J.S., Delaney, J.K., Mauzerall, D.C., Linschitz, H., "Photophysics of a Cofacial Porphyrin–Quinone Cage Molecule and Related Compounds: Fluorescence Properties, Flash Transients, and Electron–Transfer Reactions," J. Am. Chem. Soc., vol. 110, No. 11 (May 25, 1988), pp. 3610–3621.

Lindsey, J.S., Mauzerall, D.C., "Excited–State Porphyrin––Quinone Interactions at 10–A Separation," J. Am. Chem. Soc., vol. 105, No. 21 (Oct. 19, 1983), pp. 6528–6529.

Lindsey, J.S., Mauzerall, D.C., "Synthesis of a Cofacial Porphyrin–Quinone via Entropically Favored Macropolycyclization," J. Am. Chem. Soc., vol. 104, No. 16 (Aug. 11, 1982), pp. 4498–4500.

Livak, K. J., et al., "Oligonucleotides with fluorescent dyes at opposite ends provide a quenched probe system useful for detecting PCR product and nucleic acid hybridization" PCR Methods Appl. 1995, 4, 357–362.

Maliwal, Kusba, Wiczk, Johnson, and Lakowicz, "End–to–End Diffusion Coefficients and Distance Distrubitons from Fluorescence Energy Transfer Measurements: Enhanced Resolution by Using Multiple Acceptors with Different Förster Distances," *Biophysical Chemistry*, 46:273–281, May 1993.

Mathies and Huang "Capillary Array Electrophoresis: An Approach to High–Speed, High–Throughput DNA Sequencing," *Nature*, 359:167–69 (Sep. 10, 1992).

McCord, B.R., McClure, D.L., Jung, J.M., "Capillary electrophoresis of polymerase chain reaction–amplified DNA using fluorescence detection with an intercalating dye," *Journal Chromatography A*, 652, pp. 75–82, 1993.

McKeown, Lyndon and Anderson, "Generation of Mini–satellite Variant Repeat Codes on an Automated DNA Seqwuencer Using Fluorescent Dye–Labeled Primers," Biotechniques vol. 17, No. 5 pp. 901–907, Nov., 1994.

Mergny, J., Boutorine, A., Garestier, T., Belloc, F., Rougee, M., Bulychev, N., Koshkin, A., Bourson, J., Lebedev, A., Valeur, B., Thuong, N., Helene, C., "Fluorescence energy transfer as a probe for nucleic acid structures and sequences," *Nucleic Acids Research*, vol. 22, No. 6, pp. 920–928, 1994.

Middendorf, L., Bruce, J.C., Bruce, R.C., Eckles, R.D., Grone, D.L., Roemer, S.C., Sloniker, G.D., Steffens, D.L., Sutter, S.L., Brumbaugh, J.A. and Patonay, G., "Continuous, on–line DNA sequencing using a versatile infrared laser scanner–electrophoresis apparatus," *Electrophoresis*, 13:487–494, 1992.

Millar, D.P., et al., "Excited–stage quenching of dye–linked oligonucleotides" Proc. SPIE–Int. Soc. Opt. Eng. 1992, 1640, 592–598.

Montenay–Garestier et al. "Design of Bifunctional Nucleic Acid Ligands," *Molecular Basis of Specificity in Nucleic Acid–Drug Interactions*, Edited by B. Pullman and J. Jortner, Proceedings of the Twenty–Third Jerusalem Symposium on Quantum Chemistry and Biochemistry Held in Jerusalem, Israel, May 14–17, 1990, pp. 275–290.

Moore, A.L., Dirks, G., Gust, D., Moore, T.A., "Energy Transfer From Carotenoid Polyenes to Porphyrins: A Light Harvesting Antenna," Photochemistry and Photobiology, vol. 32 (1980), pp. 691–695.

Mugnier, J., et al., "Efficiency of intramolecular energy transfer in coumarin bichromophoric molecules" J. Lumin. 1985, 33, 273.

Mugnier, J., et al., "Rate of intramolecular electronic energy transfer in coumarin bichromphoric molecules. An investigation by multifrequency phase modulation fluorometry" Chem. Phys. Lettl. 1985, 119, 217.

Mujumdar, et al., "Cyanine Dye Labeling Reagents: Sulfoindicyanine Succinimidyl Esters," Bioconjugate Chemistry ,1993, 4, 105–111.

Mujumdar, S.R., Mujumdar, R.B., Grant, C.M., Waggoner, A.S., "Cyanine–Labeling Reagents: Sulfobenzindocyanine Succinimidyl Esters," Bioconjugate Chem., vol. 7 (1996) pp. 356–362.

Nakagaki, R., et al., "Photochemistry of bichromophoric chain molecules containing electron donor and acceptor moieties. Dependence of reaction pathways on the chain length and mechanism of photoredox reaction of N–(-(p–nitrophenoxy)alkyl)anilines" Chem. Phys. Lett. 1985, 121, 262–266.

Oliver, A. M., et al., "Strong effects of the bridge configuration on photoinduced charge separation in rigidly linked donor–acceptor systems" Chem. Phys. Lett. 1988, 150, 366–373.

Ozaki, H., McLaughlin, L. W., "Fluorescence resonance energy transfer between specific–labeled sites on DNA" Nucleic Acids Symposium Series 1992, 27, 67–68.

Parkhurst and Parkhurst, "Donor Acceptor Distance Distributions in a Double–Labeled Fluorescent Oligonucleotide Both as a Single Strand and in Duplexes," *Biochemistry* 34:293–300, Jan., 1995.

Parkhurst and Parkhurst, "Kinetic Studies by Fluorescence Resonance Energy Transfer Employing a Double–Labeled Oligonucleotide: Hybridization to the Oligonucleotide Complement and Single–Stranded DNA," *Biochemistry* 34:285–292, Jan., 1995.

Pispisa, B., et al., "Photophysical behavior of Poly(1–lysine) carrying Porphyrin and Naphthyl Chromophors" Biopolymers, 1994, 34, 435–442.

Prathapan, S., Johnson, T.E., Lindsey, J.S., "Building–Block Synthesis of Porphyrin Light–Harvesting Arrays," J. Am. Chem. Soc., vol. 115, No. 16 (Aug. 11, 1993), pp. 7519–7520.

Prober, Trainor, Dam, Hobbs, Robertson, Zagursky, Cocuzza, Jensen, and Baumeister "A System of Rapid DNA Sequencing with Fluorescent Chain–Terminating Dideoxynucleotides," *Science*, vol. 238, pp. 336–341 (Oct. 16, 1987).

Puers, C., Hammond, H.A., Jin, L., Caskey, C.T., Schumm, J.W.,, "Identification of Repeat Sequence Heterogenicity at the Polymorphoc Short Tandem Repeat Locus HUMTH01 [AATG]$_N$and Reassignment of Alleles in Population Analysis by Using a Locus–specific Allelic Ladder," *Am.J.Hum-.Genet.*, 53:953–958, 1993.

Ruth, J.L., Morgan, C., Pasko, A., "Linker Arm Nucleotide Analogs Useful in Oligonucleotide Synthesis," Molecular Biosystems, Inc., San Diego, CA 92121 (abstract) *DNA A Journal of Molecular Biology*, vol. 4, No. 1, Feb., 1985.

Rice, K. G., et al., "Interterminal distance and flexibility of a triantennary glycopeptide as measured by resonance energy transfer." Biochemistry 1991, 30, 6646–6655.

Rye, H.S., Quesada, M.A., Peck, K., Mathies, R.A., Glazer, A.N., "High–sensitivity two–color detection of double–stranded DNA with a confocal fluorescence gel scanner using ethidium homodimer and thiazole orange," *Nucleic Acids Research*, vol. 19, No. 2, pp. 327–333.

Sanger, Nicklen, and Coulson "DNA Sequencing with Chain–Terminating Inhibitors," *Proc. Natl.Acad.Sci.*, USA, vol. 74, No. 12, pp. 5199–5870, Dec., 1977.

Sauer, M., et al., "Design of Multiplex Dyes" Ber. Bun. Gesell. Phys. Chem. 1993, 97, 1734–1737.

Schafer, F.P., Chem. Phys. Lett. 1978, 56, 455.

Schaefer, F.P., et al., "Intramolecular TT–energy transfer in bifluorophoric laser dyes" Appl. Phys. B, 1982, B28(1) 37–41.

Scherer, T., "Comparison of flexible and rigidly bridged donor–acceptor systems–solvent induced switching between folded and extended emissive charge–transfer states" Rec. Trav. Chim. Pays–Bas. 1991, 110, 95–96.

Schnepp O., Levy, M.J., "Intramolecular energy transfer in a naphthalene–anthracene system" J. Am. Chem. Soc. 1962, 84, 172.

Scholes, G. D., et al., "Intramolecular electronic energy transfer between rigidly linked naphthalene and anthracene chromophores" J. Phys. Chem. 1993, 97, 11871–11876.

Selvin, P. R., "Fluorescence Resonance Energy Transfer" Methods Enzymol. 1995, 246, 300–334.

Selvin, P.R., Hearst, J.E.,, "Luminescence energy transfer using a terbium chelate: improvements On fluorescence energy transfer," *Proc. Natl. Acad. Sci*, USA, vol. 91, pp. 11024–10028, Oct., 1994, Biophysics.

Seth, J., Palaniappan, V., Johnson, T.E., Prathapan, S., Lindsey, J.S., Boccian, D.F., "Investigation of Electronic Communication in Multi–Porphyrin Light–Harvesting Arrays," J. Am. Chem. Soc., vol. 116, No. 23 (Nov. 16, 1994), pp. 10578–10592.

Shipchandler, M. T., et al., "4'–[Aminomethyl]fluorescein and its N–alkyl derivatives: useful reagents in immunodiagnostic techniques" Anal. Biochem. 1987, 162, 89–101.

Smith, L.M., Fung, S., Hunkapiller, M.W., Hunkapiller, T.J., Hood, L.E., "The synthesis of oligonucleotides containing an aliphatic amino group at the 5' terminus: synthesis of fluoresence DNA primers for use in DNA sequence analysis," *Nucleic Acids Research*, vol. 13, No. 7, 1985, pp. 2399–2412.

Smith, Sanders, Kaiser, Hughes, Dodd, Connell, Heiner, Kent, and Hood, "Fluorescence detection in automated DNA sequence analysis," *Nature*, vol. 321, No. 6071, pp. 674–679, Jun., 1986.

Speiser S., Katriel, J., "Intramolecular electronic energy transfer via exchange interaction in bichromophoric molecules" Chem. Phys. Lett. 1983, 102, 88–94.

Stenzel, R., et al., "Cross–reactivity of Anti–Digoxin Antibodies with Digotoxin Depends on Tracer Structure" Clin. Chem. 1992, 38, 228–2232.

Stryer "Fluorescence Energy Transfer As a Spectroscopic Ruler," *Ann. Rev. Biochem.*, 47:819–46, 1978.

Tamaki, T., "Intramolecular interaction between the phenol and indole chromophore" Bull. Soc. Chem., Jap. 1973, 46, 2527.

Theisen, McCollum, Upadhya, Jacobson, Vu, and Andrus, "Fluorescent Dye Phosphoramidite Labelling of Oligonucleotides," *Tetrahedron Letters*, vol. 33, No. 35, pp. 5033–5036, 1992.

Tian, H., et al., "Bichromophoric Rhodamine Dyes and Their Fluorescence Properties" Dyes Pigm. 1994, 26, 159–165.

Tian, H., Chen, K., "Solvent effect on the triplet lifetime of some rhodamine dyes" Dyes. Pigm. 1994, 26, 167–174.

Thornton, N.B., Schanze, K. S., "Chromophore–quencher probes for DNA" New J. Chem. 1996, 20, 791–800.

Tyagi, et al., "Molecular beacons: probes that fluoresce upon hybridization" Nature Biotechnology 1996, 14, 303–308.

Valeur, B., et al., "Calculation of the distribution of donor–acceptor distances in flexible bichromophoric molecules. Application to intramolecular transfer of excitation energy" J. Phys. Chem. 1989, 93, 6073–6079.

Vamosi, G., et al., "Fluorescence characteristics of 5–carboxytetramethylrhodamine linked covalently to the 5'end of oligonucleotides: multiple conformers of single–stranded and double–stranded dye–DNA complexes" Biophys. J. 1996, 71, 972–994.

Wagner, R.W., Brown, P.A., Johnson, T.E., Lindsey, J.S., "Self–assembly of Molecular Devices Containing a Ferrocene, a Porphyrin and a Quinone in a Triple Macrocyclic Architecture," J. Chem. Soc., Chem. Commun., No. 20 (1991), pp. 1463–1466.

Wagner, R.W., Lindsey, J.S., "A Molecular Photonic Wire," J. Am. Chem. Soc., vol. 116, No. 21 (Oct. 19, 1994), pp. 9759–9760.

Wagner, R.W., Lindsey, J.S., "Synthesis of Porphyrins Tailored with Eight Facially–Encumbering Groups. An Approach to Solid–State Light–Harvesting Complexes," Tetrahedron, vol. 50, No. 38 (1994), pp. 11097–11112.

Wagner, R.W., Ruffing, J., Breakwell, B.V., Lindsey, J.S., "Synthesis of Facially–Encumbered Porphyrins, An Approach to Light–Harveting Antenna Complexes," Tetrahedron Letters, vol. 32, No. 14 (1991), pp. 1703–1706.

Wang, Y., Ju, J., Carpenter, B.A., Atherton, J.M., Sensabaugh, G.F., Mathies, R.A.,, Rapid Sizing of Short Tandem Repeat Alleles Using Capillary Array Electrophoresis and Energy–Transfer Fluorescent Primers, *Anal. Chem.* 67, 1197–1203, 1995.

Wasielewski, M.R., Liddell, P.A., Barrett, D., Moore, T.A., Gust, D., "Ultrafast carotenoid to pheophorbide energy transfer in a biomimietic model for antenna funciton in photosynthesis," Nature, vol. 322, (Aug. 1986), pp. 570–572.

Weber, G., et al., Fluorescence excitation spectrum of organic compounds in solution Part I. Systems with quantum yield independent of exciting wavelength. Trans. Faraday Soc. 1958, 54, 640.

Weber, J.L., May, P.e., "Abundant Class of Human DNA Polymorphisms Which Can Be Typed Using the Polymerase Chain Reaction," *Am.J.Hum.Genet.*, 44:388–396, 1989.

Wei, A., Blumenthal, D.K., Herron, J.N., "Antibody–Mediated Fluorescence Enhancement Based on Shifting the Intermolecular Dimer—Monomer Equilibrium of Fluorescent Dyes," *Anal. Chem.*, 66, 1500–1506, 1994.

Weiss, S., et al., "Probing the interaction between single molecules: fluorescence resonance energy transfer between a single donor and a single acceptor" Conference Title: QELS '96. Summaries of Papers Presented at the Quantum Electronics and Laser Science Conference. vol. 10 1996 Technical Digest Series. Conference Edition (IEEE Cat. No. 96CH35902).

Wong, L.C., Ashizawa, T., Monckton, D.G., Caskey, C.T., Richards, C.S., "Somatic Heterogenicity of the CTG Repeat in Myotonic Dystrophy Is Age and Size Dependent", *Am.J.Hum. Genet.*, 56:114–122, 1995.

Wu P., "Resonance energy transfer: methods and applications" Anal. Biochem. 1994, 218, 1–13.

Yang, J., Winnik, M. A., "Fluorescence energy transfer studies in a cross–linked polyurethane network" Can. J. Chem. 1995, 73, 1823–1830.

Yingshen, W., Schanze, K. S., "Photochemical probes of intramolecular electron and energy transfer transfer" J. Chem. Phys. 1993, 176, 305–319.

Yuan, P., "Photophysical behavior of bichromophores and energy transfer–based indicators" Ph.D. Dissertation, 1991, Tufts University.

Zeng, Z., et al., "Fluorescence energy–transfer cyanine heterodimers with high affinity for double–stranded DNA. II. Applications to multiplex restriction fragment sizing " Anal. Biochem. 1995, 231, 256–260.

Zerylnick, C., Torroni, A., Sherman, S.L., Warren, S.T., "Normal Variation at the Myotonic Dystrophy Locus in Global Human Populations," *Am.J.Hum.Genet.*, 56:123–130, 1995.

Zhu, Z., Chao, J., Yu, H., Waggoner, A.S., "Directly labeled DNA probes using fluorescent nucleotides with different length linkers," Nucleic Acids Research, Vo. 22, No. 16 (Aug. 25, 1994) pp. 3418–3422.

Zhu, H., Clark, S.M., Benson, S.C., Rye, H.S., Glazer, A.N., Mathies, R.A., "High–Sensitivity Capillary Electrophoresis of Double–Stranded DNA Fragments Using Monomeric and Dimeric Fluorescent Intercalating Dyes," *Anal.Chem.*, vol. 66, No. 13, Jul. 1, pp. 1941–1948, 1994.

Civil Docket for Case #: 97–CV–4203, U.S. District Court for the Northern District of California (S.F.) pp. 1–59.

Multi–Page Transcript of Deposition of Richard P. Haugland, Ph.D., taken Sep. 15–16, 1998.

Initial Disclosure Of Asserted Claims Pursuant To Civil L.R. 16–7, dated Mar. 12, 1998.

Initial Disclosure Of Prior Art Pursuant To Civil Local Rule 16–7(D), dated May 21, 1998.

Notice Of Plaintiff's Claim Chart Pursuant To Civil Local Rule 16–9, dated Jun. 03, 1998.

Response To APBI's First Set Of Requests For Documents And Things, dated Jun. 22, 1998.

Local Rule 16–7(E) Initial Disclosure Of Prior Art, dated Jun. 24, 1998.

Response To APBI's First Set Of Requests For Admission Nos. 1–87, dated Jun. 29, 1998.

Response To APBI's Second Set Of Requests For Admission Nos. 88–107, dated Jun. 29, 1998.

Notice Of Plaintiff's Claim Chart Pursuant To Civil Local Rule 16–10, W/Attached Exhibit 1: Proposed Claim Construction Statement For U.S. Patent No. 5,688,648, dated Jul. 28, 1998.

Amersham's Response To First Set Of Requests For Production Of Documents And Things To The Perkin–Elmer Corporation, dated Aug. 10, 1998.

Amended Civil L.R. 16–7(D) Initial Disclosure Of Prior Art For U.S. Patent No. 5,688,648, dated Aug. 17, 1998.

Applied Biosystem's Civil L.R. 16–9(B) Response Chart For U.S. Patent No. 5,688,648—Exhibit A—Applied Biosystems' Civil Local Rule 16–9(B)(1)–(3) Response Chart For The '648 Patent, dated Sep. 17, 1998.

Applied Biosystems' Civil L.R. 16–10(B) Response Chart for U.S. Patent No. 5,688,648—Exhibit A—Applied Biosystems' Civil Local Rule 16–10(B) Chart, dated Sep. 30, 1998.

Applied Biosystems' Response To Amersham's First Set Of Interrogatories, dated Nov. 09, 1998.

Perkin–Elmer's Updated Responses To Amersham's First Set Of Requests For Documents And Things Nos. 1–6, 10, 13, 16, 17, And 20–22, dated Sep. 24, 1999.

Perkin–Elmer's Responses to Amersham's Second Set Of Requests For Documents And Things Nos. 1–58, dated Sep. 27, 1999.

Perkin–Elmer's Responses To Amersham's Third Set Of Requests For Production Of Documents And Things Nos. 1–34, dated De. 20, 1999.

Perkin–Elmer's Amended Civil L.R. 16–9(B) Response Chart For U.S. Patent No., 5,688–648; Exhibit A—Perkin–Elmer's Corrected Civil L.R. 16–9(B) Response Claim Chart For U.S. Patent 5,688,648; Exhibit B—Perkin–Elmer's Supplemental Civil L.R. 16–9(B) Response Claim Chart For U.S. Patent No. 5,688,648, dated Feb. 08, 2000.

Amersham Pharmacia Biotech, Inc.'s Supplemental Initial Disclosure Pursuant to Local Rule 16–5 And Fed.R.Civ.P. 26(a)(1), dated Mar. 27, 2000.

Initial Disclosure Of Plaintiff Amersham Pharmacia Biotech, Inc., Pursuant To Civil Local Rule 16–7 (Supplemented), dated Mar. 27, 2000.

Amersham Pharmacia Biotech, Inc.'s Notice Of Supplemented Civil Local Rule 16–9 Claim Chart, dated Mar. 27, 2000.

Amersham Pharmacia Biotech, Inc.'s Supplemental Response To The First Set Of Requests For Production Of Documents And Things To The Perkin–Elmer Corporation, dated Mar. 27, 2000.

Perkin–Elmer Supplemental Responses To Amersham's Requests For Admission Nos. 42 And 43, dated Apr. 26, 2000.

Perkin Elmer Corporation's Responses To Amersham Pharmacia Biotech, Inc.'s Revised Requests For Admission Nos. 19–24, dated Apr. 26, 2000.

Perkin–Elmer's Responses To Amersham's Second Set Of Interrogatories (No. 8), dated May 01, 2000.

Perkin–Elmer's Responses To Amersham's Fourth Set Of Requests For Production Of Documents And Things (Nos. 1–34), dated May 01, 2000.

Amersham Pharmacia Biotech, Inc.'s Answers To Perkin–Elmer's First Set Of Interrogatories (Nos. 1–6), dated May 31, 2000.

Perkin–Elmer's Supplemental Responses To Amersham's First Request For Admission (Nos. 26–28, 30–33, 35, 37, 39, 41, 44–51, 53–55, 64–68 And 70–71); Proof Of Service, dated Jun. 08, 2000.

Amersham Pharmacia Biotech, Inc.'s Supplemental Answer To Perkin–Elmer's Interrogatory No. 2, dated Jun. 16, 2000.

Perkin–Elmer's Responses To Amersham's Fifth Set Of Requests For Production Of Documents (Nos. 1–26); Proof Of Service, dated Jul. 03, 2000.

Perkin–Elmer's Responses To Amersham's Sixth Set Of Requests For Production Of Documents (Nos. 1–8), dated Jul. 10, 2000.

Perkin–Elmer's Amended Responses To Amersham's Fifth Set Of Requests For Production Of Documents (Nos. 1–26), dated Jul. 19, 2000.

Amersham's Responses To Perkin–Elmer's Second Set Of Request For Production Of Documents, dated Jul. 24, 2000.

Amersham's Responses To Perkin–Elmer's Third Set Of Request For Production Of Documents, dated Aug. 30, 2000.

Perkin–Elmer's Supplemental Responses To Amersham's First Request For Admissions (Nos. 25, 82 And 38), dated Jul. 25, 2000.

Amersham's Answers To Perkin–Elmer's First Set Of Requests For Admission To Amersham (Nos. 1–31), dated Aug. 2, 2000.

The Perkin–Elmer Corporation's Supplemental Responses To Amersham Pharmacia Biotech, Inc.'s First Set Of Interrogatories (Nos. 1–7), dated Aug. 04, 2000.

Amersham Pharmacia Biotech, Inc.'s Responses To Perkin–Elmer's Second Set Of Interrogatories (Nos. 7–12), dated Aug. 7, 2000.

Perkin–Elmer's Responses To Amersham's Seventh Set Of Requests For Production Of Documents (Nos. 1–35), dated Aug. 18, 2000.

Amersham Pharmacia Biotech, Inc.'s Supplemental Answers To Perkin–Elmer's First Set Of Interrogatories (Nos. 4–6), dated Aug. 18, 2000.

Perkin–Elmer's Responses To Amersham's Eighth Set Of Requests For Production Of Documents (Nos. 1–5), dated Aug. 18, 2000.

Amersham's Supplemental Answers To Perkin–Elmer's Requests For Admission To Amersham (Nos. 1–7), dated Aug. 25, 2000.

Amersham Pharmacia Biotech, Inc.'s Responses To Perkin–Elmer's Third Set Of Interrogatories (Nos. 13–16), dated Sep. 7, 2000.

Perkin–Elmer's Responses To Amersham's Fourth Set Of Interrogatories (Nos. 18–25), dated Sep. 7, 2000.

Perkin–Elmer's Responses To Amersham's Reinstated First Set Of Requests For Admissions (Nos. 34, 36, 38, 40, 52, 56–63, 69, 74, 76, And 78–79), dated Sep. 12, 2000.

Amersham Pharmacia Biotech, Inc.'s Revised Supplemental Answers To Perkin–Elmer's First Set Of Interrogatories (Nos. 4–6), dated Sep. 20, 2000.

Amersham Pharmacia Biotech, Inc.'s Second Revised Supplemental Answer To Perkin–Elmer's First Set Of Interrogatories (Nos. 4–6), dated Sep. 22, 2000.

Perkin–Elmer's Updated Indentification Of References Pursuant To 35 U.S.C. § 282, dated Jun. 07, 2001.

Complaint For Infringement Of USP 5,688,648 And Demand For Jury, dated Nov. 18, 1997.

Second Amended Complaint For Infringement Of USP '648, dated Mar. 25, 1998.

Answer To Amersham's Second Amended Complaint, Counterclaim, dated Apr. 20, 1998.

Reply To Counterclaim, dated May 05, 1998.

Plaintiff Amersham Pharmacia Biotech, Inc.'s Initial Brief Re Claim Construction Of U.S. Patent No. 5,688,648, dated Oct. 18, 1999.

Palintiff Amersham Pharmacia Biotech, Inc.'s Revised Initial Brief Re Claim Construction Of U.S. Patent No. 5,688, 648, dated Oct. 25, 1999.

Perkin–Elmer's Responsive Claim Construction Brief Regarding U.S. Patent No. 5,688,648, dated Nov. 03, 1999.
Amersham's Reply Brief On Claim Construction, dated Nov. 10, 1999.
Amersham's Post–Hearing Brief On Claim Construction, dated Jan. 10, 2000.
Perkin–Elmer's Post–Hearing Claim Construction Brief Regarding U.S. Patent No. 5,688,648, dated Jan. 10, 2000.
Magistrate Judge's Recommended Order Re: Claim Construction Of U.S. Patent No. 5,688,648, dated Feb. 28, 2000.
Order Correcting Typographical Error In Magistrate Judge's Recommended Order Re: Claim Construction Of U.S. Patent No. 5,688,648, dated Mar. 03, 2000.
Perkin–Elmer's Motion For De Novo Determination, dated Mar. 13, 2000.
Objection To Magistrate Judge's Recommended Order Re: Claim Construction Of U.S. Patent No. 5,688,648, dated Mar. 13, 2000.
Amersham Pharmacia Biotech, Inc.'s Fed.R.Civ.P. 72(B) Reply To Perkin–Elmer's Objection To Magistrate Judge Infante's Recommended Order Re: Claim Construction Of U.S. Patent No. 5,688,648, dated Apr. 2, 2000.
Amersham Pharmacia Biotech, Inc.'s Opposition To The Perkin–Elmer Corporation's Motion For De Novo Determination, dated Apr. 3, 2000.
Order Re: De Novo Determination, dated May 19, 2000.
Perkin–Elmer's Opposition To Amersham's Motion For Summary Judgment Of Infringement Of The '648 Patent, dated Jul. 21, 2000 and Sep. 22, 2000.
Perkin–Elmer's Expedited Motion To Amend Answer And Counterclaim To Add Inequitable Conduct Allegations, dated Sep. 18, 2000.
Defendant's First Amended Answer To Amersham's Second Amended Complaint And First Amended Counterclaim, dated Oct. 5, 2000.
Perkin–Elmer's Motion For Summary Judgement Of Invalidity Of U.S. Patent No. 5,688,648 Based On Anticipation By The Haughland Reference, dated Nov. 13, 2000.
Perkin–Elmer's Motion For Summary Adjudication That The Kanbara Reference Discloses And Enables Each Of The Elements Of Claims 1–3 Of U.S. Patent No. 5,688,648, dated Nov. 13, 2000.
Reply In Support Of Perkin–Elmer's Motion For Summary Judgment Of Invalidity Of U.S. Patent No. 5,668,648 Based On Anticipation By The Haughland Reference, dated Dec. 6, 2000.
Defendant's First Amended Answer To Amersham's Second Amended Complaint And First Amended Counterclaim, dated Dec. 18, 2000.
Order (Re: Request To Focus Invalidity Arguments), dated Dec. 18, 2000.
Memorandum And Order Re: Infringement, dated Dec. 22, 2000.
Perkin–Elmer's Identification Of References Pursuant To 35 U.S.C. § 282, dated Dec. 29, 2000.
Amersham Pharmacia Biotech, Inc.'s Answer To Perkin–Elmer's First Amended Counterclaim, dated Jan. 3, 2001.
Plaintiff Amersham Pharmacia Biotech, Inc.'s Brief Re: Construction Of The Claim Term "Backbone Chain," dated Jan. 3, 2001.
Order Re: "Backbone Chain," dated Jan. 3, 2001.
To Honorable C. Breyer Re: Construction Of Claim Term "Backbone Chain" In U.S. Patent No. '648, dated Jan. 8, 2001.
Order Re: More Definite Claim Chart And Response To Claim Construction Statement, dated Jan. 29, 2001.
Third Amended Complaint For Infringement Of United States Patent No. 5,688,648, dated Feb. 1, 2001.
Defendant's Answer To Amersham's Third Amended Complaint And Second Amended Counterclaim, dated Feb. 15, 2001.
Andersson et al., "In Vitro Biotransformation of Glucocorticoids in Liver and Skin Homogenate Fraction from Man, Rat and Hairless Mouse," *J. Steroid Biochem.*, vol. 16, pp. 787–795 (1982).
S. Bondesen et al., "Absorption of 5–aminosalicyclic from colon and rectum," *Br. J. Clin. Pharmac.*, (1988), 25, 269–272.
Bostrom et al., "Cellular Pharmacology of 6–Mercaptopurine in Acute Lumphoblastic Leukemia," *The American Journal of Pediatric Hematology/Oncology*, 15(1): 80–86 (1993).
A. H. Chalmers, "Studies on the Mechanism of Formation of 5–Mercapto–1–Methyl–4–Nitroimidazole, A Metabolite of the Immunosuppressive Drug Azathioprine," *Biochemical Pharmacology*, vol. 23, pp. 1891–1901.
Laurie D. DeLeve et al., "Glutathione Metabolism and Its Role in Hepatotoxicity," *Pharmac. Ther.*, vol. 52, pp. 287–305 (1991).
B. Norlander et al., "Pharmacokinetics of a 5–aminosalicylic acid enteric–coated tablet in patients with Crohn's disease or ulcerative colitis and in healthy volunteers", *Ailment. Pharmacol. Therap.*, (1990) 4, 497–505.
Y. Kato et al., "Rectal bioavailability of 6–mercaptopurine in children with acute lymphobastic leukaemia: partial avoidance of "first–pass" metabolism", *Eur. J. Clin. Pharmacol.*, (1992) 42:619–622.
Lynne Lennard et al., "Pharmacogenetics of acute azathioprine toxicity: Relationship to thiopurine methyltransferase genetic polymorphism," *Clinical Pharmacology & Therapeutics*, vol. 46, No. 2, (1989), pp. 149–154.
L. Lennard, "The clinical pharmacology of 6–mercaptopurine," *Eur. J. Clin. Pharmacol.*, (1992) 43:329–339.
J. Liliemark et al., "Determination of Plasma Azathioprine and 6–Mercaptopurine in Patients with Rehumatoid Arthritis Treated with Oral Azathioprine," *Therapeutic Drug Monitoring*, 12:339–343 (1990).
Kenneth W. Schroeder et al., "Coated Oral 5–Aminosalicyclic Acid Therapy for Mildly to Moderately Active Ulcerative Colitis," *The New England Journal of Medicine*, vol. 317, No. 26, pp. 1625–1629.
J. Herman et al. , "Modified Starches as Hydrophilic Matrixes for Controlled Oral Delivery. I. Production and Characterization of Thermally Modified Starches," *Int. Journal of Pharmaceutics*, 56 (1989) 51–63.
Marvin M. Schreiber et al., "Bioactivity of Controlled Release Formulations of Starch–Encapsulated EPTC," *Journal of Controlled Release*, 7 (1988) 237–242.
TJH Clark et al., "Safety of Inhaled Corticosteroids," International Symposium on Corticosteroid Treatment in Allergic Airway Diseases, Oct. 1–2, 1981, European Journal of Respirtory Diseases, Supp. No. 122, vol. 63 (1982).
R.M. Weinshilboum, "Methylation pharmacogenetics: thiopurine methyltransferase as a model system," *Xenobiotica*, 1992, vol. 22, Nos. 9/10, 1055–1071.
W.J. Sandbord, "Azathiprine: State of the Art in Inflammatory Bowel Disease", *Scandinavian Journal of Gastroenterology*, vol. 33, Supp. 225, 1998, pp. 92–99.

SL Wolman, "Use of Oral Budesonide in a Patient with Small Bowel Crohn's Disease and Previous Psudotumor Cerebri Secondary to Steroids," *Scandinavian Journal of Gastroenterology*, vol. 24, Supp. 158, 1989, pp. 146–147.

S. Agrawal and P.C. Zamecnik, *Nucleic Acids Research* (Aug. 1990) 18(18): 5419–5423.

U. Asseline et al., *EMBO Journal* (Jan. 1984) 3(4): 795–800.

D. Bergstrom, et al., *Synlett: Accounts and Rapid Communications in Synthetic Organic Chemistry* (Mar. 1992) 3: 179–188.

S.C. Benson et al., *Nucleic Acids Research* (Nov. 1993) 21(24): 5720–5726.

S.C. Benson et al., *Nucleic Acids Research* (Nov. 1993) 21(24): 5727–5735.

J. Brumbauch et al., *Proc. Natl. Acad Sci. USA* (Aug. 1998) 85: 5610–5614.

R.A. Cardullo et al. *Proc. Natl. Acad. Sci. USA* (Dec. 1998) 85: 8790–8794.

R.M. Clegg, *Methods in Enzymology* (1992) 211: 353–389.

J.P. Cooper and P.J. Hagerman, *Biochemistry* (Jul. 1990) 29: 9261–9268.

J.M. Drake et al. *Science* (Mar. 1991) 251: 1574–1579.

R.P. Haugland, Small Business Innovation Research Program, Phase I Grant Application, submitted Dec. 13, 1985, and associated work.

R.P. Haughland, Small business Innovation Research Program, Phase II Grant Application, proposed period Mar. 1, 1988–Feb. 28, 1991.

R.P. Haugland, "Fluorescence–Detected DNA Sequencing," Dept. of Energy, Research Abstracts for 1988.

R.P. Haugland, U.S. Dept. of Energy, Grant Application, dated Oct. 31, 1987.

R.P. Haugland, "Fluorescence–Detected DNA Sequencing, Final Technical Report," Grant No. DE–FG06–88ER60684, Sep. 29, 1990.

M.J. Heller et al. *Federation Proceedings* (Jun. 1987) 46(6): Abstract.

H–C. Kang et al., "Human Genome 1989–90 Program Report" (Mar. 1990) p. 55.

L.G. Lee et al. *Nucleic Acids Research* (Apr. 1992) 20(10): 2471–2483.

L.G. Lee et al. *Nucleic Acids Research* (Jun. 1993) 21(16): 3761–3766.

P.S. Nelson et al. *Nucleic Acids Research* (Aug. 1989) 17(18): 7187–7194.

H. Ozaki and L.W. McLaughlin, *Nucleic Acids Research* (Sep. 1992) 20(19): 5205–5214.

S. Sixou et al., *Nucleic Acids Research* (Dec. 1993) 22(4): 662–668.

L. Stryer and R.P. Haugland, *Proc. N.A.S.* (1967) 38:719–726.

H. Tanke, "What's New From the Field: Current Developments in Flow Cytometry and Fluorescent Labels" 63–65.

* cited by examiner

The color of the top peak indicates a particular base, thus allowing direct assignment of the sequence.

Green = C (F10F);   Orange = A (F10J);   Red = T (F10R);   Black = G (F10T)

PROBES LABELED WITH ENERGY TRANSFER COUPLED DYES

CROSS-REFERENCE TO RELATED APPLICATIONS

This application is a continuation of application Ser. No. 08/646,861 filed May 8, 1996, now U.S. Pat. No. 6,028,190, which is a continuation-in-part of application Ser. No. 08/411,573 filed Mar. 27, 1995, now abandoned, and a continuation-in-part of application Ser. No. 08/410,808 filed Mar. 27, 1995, now U.S. Pat. No. 5,707,804, both applications Ser. Nos. 08/411,573 and 08/410,808 being continuations-in-part of application Ser. No. 08/189,924 filed Feb. 1, 1994, now U.S. Pat. No. 5,654,419. The disclosures of all applications and patents cited in this paragraph are herein incorporated by reference.

INTRODUCTION

1. Technical Field

The field of this invention is fluorescent labeled primers and their use.

2. Background

There is an increasing demand to be able to identify and quantify components of mixtures. The greater the complexity of the mixture, the greater the interest in being able to simultaneously detect a plurality of the components present. As illustrative of this situation is DNA sequencing, where it is desirable to efficiently excite from one to four fluorescently tagged components with a laser source, while providing for fluorescent signal emission at a plurality of distinctive wavelengths, where the fluorescence signals should be as intense as possible. In this situation, the different labels should not adversely affect the electrophoretic mobility of the sequences to which they are attached.

Currently, there are four methods used for automated DNA sequencing: (1) the DNA fragments are labeled with one fluorophore and then the fragments run in adjacent sequencing lanes (Ansorge et al., *Nucleic Acids Res.* 15, 4593–4602 (1987); (2) the DNA fragments are labeled with four different fluorophores and all the fragments are electrophoretically separated and detected in a single lane (Smith et al., *Nature* 321, 674–679 (1986); (3) each of the dideoxynucleosides in the termination reaction is labeled with a different fluorophore and the four sets of fragments are run in the same lane (Prober et al., *Science* 238, 336–341 (1987); or (4) the sets of DNA fragments are labeled with two different fluorophores and the DNA sequences coded with the dye ratios (Huang et al., *Anal. Chem.* 64, 2149–2154 (1992).

All of these techniques have significant deficiencies. Method 1 has the potential problems of lane-to-lane variations in mobility, as well as a low throughput. Methods 2 and 3 require that the four dyes be well excited by one laser source and that they have distinctly different emission spectra. In practice, it is very difficult to find two or more dyes that can be efficiently excited with a single laser and that emit well separated and intense fluorescent signals.

As one selects dyes with distinctive red-shifted emission spectra, their absorption maxima will also move to the red and all the dyes can no longer be efficiently excited by the same laser source. Thus, the detection sensitivity for these dyes will suffer. Also, as more different dyes are selected, it becomes more difficult to select all the dyes such that they cause the same mobility shift of the labeled molecules.

It is therefore of continued interest that improved labels be developed which have strong absorption at a common wavelength, have a high quantum yield for fluorescence, have intense fluorescence signals and have a large Stokes shift of the emission.

RELEVANT LITERATURE

U.S. Pat. No. 4,996,143 reports the preparation of oligonucleotide probes comprising donor and acceptor fluorophores designed for the detection of complementary DNA target sequences by hybridization to form labeled double-strand DNA fragments. These probes were specifically labeled in the middle of the probe, explicitly excluding the 5' or 3' end base unit.

Smith et al., Nucleic Acids Research (1986) 321:674–679 reports the synthesis of oligonucleotides having an aliphatic amino group at the 5' terminus, as well as the preparation of fluorescent derivatives thereof, containing only a single fluorescent label. cl SUMMARY OF THE INVENTION Labels comprising at least one pair of fluorophores, wherein a pair is comprised of a donor and acceptor fluorophore, in energy transfer relationship, and methods for their use, are provided. To generate the labels, pairs or families of fluorophores are bound to a backbone, particularly a nucleic acid backbone, where one member of the pair is bonded to a terminus of the backbone. The range of distances between donor and acceptor fluorophores is chosen to ensure efficient energy transfer, and can be modulated to affect the label mobility. The subject labels find particular use as primers in nucleotide chain extension applications, such as sequencing, PCR and the like.

BRIEF DESCRIPTION OF THE SCHEMES

Figure 1:
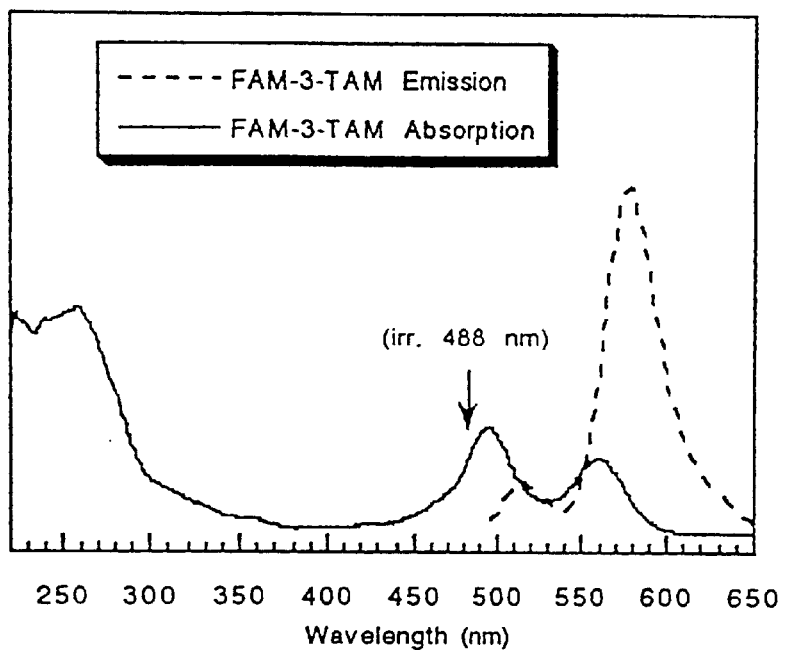
FIG. 1 is a graph of the absorption and emission spectra of FAM-3-TAM in 1×TBE.

SCHEME 1. Structures of twenty energy transfer (ET) primers and a representative synthetic scheme for the preparation of F3T.

SCHEME 2. Structures of the four energy transfer (ET) primers and a representative synthetic scheme for the preparation of F6R. The fluorescent primers are labeled with a common fluorescein donor (F) at the 5' end and either a second fluorescein or a rhodamine (R) acceptor at the indicated locations of a modified T in the sequence. The number of nucleotides between the two fluorophores is indicated in the primer designation.

SCHEME 3. Structures of the PCR primers used for the amplification of the VWFA, THO1, TPO and CSF loci. The fluorescent primers are labeled with a common fluorescein donor (F) at the 5' end and either a second fluorescein or a rhodamine (R) acceptor at the indicated locations of a modified T in the sequence. The number of nucleotides between the two fluorophores is indicated in the primer designation.

DESCRIPTION OF SPECIFIC EMBODIMENTS

Novel fluorescent labels, combinations of fluorescent labels, and methods of their use, are provided. The subject fluorescent labels comprise at least one donor and acceptor fluorophore, which may be the same or different, bound to a polymeric backbone in energy transfer relationship, where one of the fluorophores is positioned at one of the termini of the polymeric backbone. The range of distances between donor and acceptor fluorophores is chosen to ensure efficient energy transfer, and can be modulated to affect the label mobility. In the case where the fluorophores are identical, the range of distances is chosen so as to maximize the fluorescence intensity. The subject labels find particular use as primers in nucleotide chain extension applications, such as sequencing, PCR and the like.

The subject labels will comprise one or more pairs of fluorophores, where a donor and acceptor fluorophore make a pair. With one exception where the fluorophores are the same, the pair or pairs of fluorophores have overlapping spectra, where the donor emission overlaps the acceptor absorption, so that there is energy transfer from the donor to acceptor fluorophore. It is not essential that the excited or donor fluorophore actually fluoresce, it being sufficient that the excited fluorophore be able to efficiently absorb the excitation energy and efficiently transfer it to the emitting or acceptor fluorophore.

The donor fluorophores in the different families of fluorophores may be the same or different, but will be able to be excited efficiently by a narrow bandwidth source. The emitting or accepting fluorophores will be selected to be able to receive the energy from donor fluorophores and emit light, which will be distinctive and detectably different. Therefore, one will be able to distinguish between the components of the mixture to which the different labels have been bound.

Usually the donor fluorophores will absorb in the range of about 350–800 nm, more usually in the range of about 350–600 nm or 500–750 nm, while the acceptor fluorophores will emit light in the range of about 450–1000 nm, usually in the range of about 450–800 nm. One may have more than a pair of absorbing molecules, so that one may have 3 or more molecules, where energy is transferred from one molecule to the next at higher wavelengths, to greatly increase the difference in wavelength between absorption and observed emission.

The fluorophores may be selected so as to be from a similar chemical family, such as cyanine dyes, xanthenes or the like. Thus, one could have the donors from the same chemical family, each donor-acceptor pair from the same chemical family or each acceptor from the same family.

Among the members of the pairs of the fluorophores, one of the fluorophore members will be located at one of the termini of the label, with the other member or members being located at an internal site along the polymeric backbone of the label. In other words, either the donor or acceptor fluorophore may be located at one terminus of polymeric backbone while the other fluorophore member of the pair will be bonded to a non-terminal monomeric unit of the polymeric backbone. Thus, where the donor is bonded to one of the label termini, the acceptor will be bonded at an internal site along the polymeric backbone of the label, and vice versa where the acceptor is bonded to one of the label termini.

In the subject labels, the two fluorophores will be bonded to a backbone or chain, usually a polymeric chain, where the distance between the two fluorophores may be varied. As mentioned above, the distance between the donor and acceptor members of the pair will provide for efficient transfer of energy from the donor to the acceptor. In terms of monomeric units of the polymeric backbone chain, the distance between the pairs of fluorophores will be at least about 2, usually at least about 3, and may be as great as 10 or greater, but will usually be less than about 20, more usually less than about 15.

Various chains or backbones may be employed, where the backbones will comprise monomeric units having bases selected from purines, pyrimidines and hybridizing analogues thereof, such as nucleic acids, both DNA and RNA, modified nucleic acids, e.g. where oxygens may be substituted by sulfur, carbon, or nitrogen, phosphates substituted by sulfate or carboxylate, etc., polypeptides, e.g. peptide nucleic acids (Nielsen et al., Science (1991) 254:1497–1500; Hanvey et al., Science (1992) 258: 1481–1485), polysaccharides, various groups which may be added stepwise, such as di-functional groups, e.g. haloamines, or the like. The fluorophores may be substituted as desired by appropriate functionalization of the various building blocks, where the fluorophore may be present on the building block during the formation of the label, or may be added subsequently, as appropriate. Various conventional chemistries may be employed to ensure that the appropriate spacing between the two fluorophores is obtained.

It is found that the spacing between the two fluorophores will affect the mobility of the label. Therefore, one can use different dye pairs and, by varying the distance between the different dye pairs within a range which still permits good energy transfer, provide for substantially constant mobility for the labels. The mobility is not related to the specific spacing, so that one will empirically determine the effect of the spacing on the mobility of a particular label. However, because of the flexibility in the spacing of the fluorophores in the labels, by synthesizing a few different labels with different spacings and different dye pairs, one can now provide for a family of fluorescent labels, which share a common excitation, that have strong and distinctive emission and a substantially common mobility. Usually, the mobility will differ by not more than about 20% of each other, preferably not more than about 10% of each other, and more preferably within about 5% of each other, when used in a particular separation. The mobility may usually be determined by carrying out the separation of the labels by themselves or the labels bound to a common molecule which is relevant to the particular separation, e.g. a nucleic acid molecule of the appropriate size, where one is interested in sequencing. Relative mobility shift can also be adjusted by changing the dyes or dye derivatives used as donors and acceptors.

As discussed above, a wide variety of fluorescent dyes may find application as the fluorophores in the subject labels. These dyes will fall into various classes, where combinations of dyes may be used within the same class or between different classes. Included among the classes are dyes such as the xanthene dyes, e.g. fluoresceins and rhodamines; coumarins, e.g. umbelliferone; benzimide dyes, e.g. Hoechst 33258, phenanthridine dyes; e.g. Texas Red and ethidium dyes; acridine dyes; Bodipy; cyanine dyes, such as thiazole orange, thiazole blue, Cy 5, and Cyfr; carbazole dyes; phenoxazine dyes; porphyrin dyes; quinoline dyes; or the like. Thus, the dyes may absorb in the ultraviolet, visible or infra-red ranges. For the most part, the fluorescent molecules will have a molecular weight of less than about 2 kDal, generally less than about 1.5 kdal.

The energy donor should have strong molar absorbance coefficient at the desired excitation wavelength, desirably greater than about $10^4$, preferably greater than about $10^5$ $cm^{-1}M^{-1}$. The excitation maximum of the donor and the emission maximum of the acceptor (fluorescer) will be separated by at least 15 nm or greater. The spectral overlap integral between the emission spectrum of the donor chromophore and the absorption spectrum of the acceptor chromophore and the distance between the chromophores will be such that the efficiency of energy transfer from donor to acceptor will range from 20% to 100%.

Separation of the donor and acceptor based on number of atoms in the chain will vary depending on the nature of the backbone, whether rigid or flexible, involving ring structures or non-cyclic structures or the like. Generally the number of atoms in the chain (the atoms in the ring structures will be counted as the lowest number of atoms around one side of the ring for inclusion in the chain) will be below about 200, usually below about 150 atoms, preferably below about 100, where the nature of the backbone will influence the efficiency of energy transfer between donor and acceptor.

While for the most part, pairs of fluorophores will be used, there can be situations where up to four different, usually not more than three different, fluorophores bound to the same backbone may find use. By using more fluorophores, one may greatly extend the Stokes shift, so that one may excite in the visible wavelength range and emit in the infra-red wavelength range, usually below about 1000 nm, more usually below about 900 nm. Detecting light in the infra-red wavelength range has many advantages, since it will not be subject to interference from Raman and Rayleigh light resulting from the excitation light. In order to maintain the mobility constant, one may use the same number of fluorophores on the labels, having a multiplicity of the same fluorophore to match the number of fluorophores on labels having different fluorophores for the large Stokes shift.

Of particular interest are labels comprising a donor and acceptor fluorophore bonded to a nucleic acid backbone, where the labels will generally have at least about 10 nucleotides and not more than about 50 nucleotides, usually not more than about 30 nucleotides. In these particular labels, one of the fluorophores (the first fluorophore), where the first fluorophore may be either the donor or acceptor fluorophore, will be bonded to the 5' terminus of the label, with the other fluorophore(s) being bonded to an internal nucleotide 3' to the first fluorophore, where the number of the nucleotides between the donor and acceptor fluorophores will range from about 2 to 15, usually from about 3 to 10 and more usually from about 4 to 10.

The fluorophores will usually be joined to the nucleotides by a convenient linking arm of from about 2 to 20, usually 4 to 16 atoms in the chain. The chain may have a plurality of functionalities, particularly non-oxo-carbonyl, more particularly ester and amide, amino, oxy, and the like. The chain may be aliphatic, alicyclic, aromatic, heterocyclic, or combinations thereof, usually comprising carbon, nitrogen, oxygen, sulfur, or the like in the chain.

For the most part the fluorophores will have maximum emission wavelengths that differ by 100 nm or less, where the maximum emission wavelengths of the donor and acceptor fluorophores will typically differ by at least about 10 nm, usually at least about 15 nm, more usually at least about 20 nm, but will generally differ by less than about 100 nm, usually less than about 25 nm.

For the subject labels, the donor and acceptor fluorophores are drawn from classes of compounds such as phenylxanthene dyes, cyanine dyes, phenanthridine dyes, aminonaphthylimide derivatives, and the like. Of particular interest is FAM as a common donor with JOE, TAMRA, ROX, 6-carboxyrhodamine-6G, or 5-carboxyrhodamine-6G as alternative acceptors in donor/acceptor pairs. Under some conditions, e.g. where it is desired that the excitation wavelength closely correlate to the maximum absorption wavelength of the donor molecule, cyanine donors may be preferred.

The subject labels may be prepared using any convenient means. A large number of nucleosides are available, which are functionalized, and may be used in the synthesis of a polynucleotide. By synthesizing the subject nucleic acid labels, one can define the specific sites at which the fluorophores are present. Commercially available synthesizers may be employed in accordance with conventional ways, so that any sequence can be achieved, with the pair of fluorophores having the appropriate spacing.

The subject labels find use in a variety of applications, including various separation techniques, such as electrophoresis, chromatography, or the like, where one wishes to have optimized spectroscopic properties, high sensitivity and comparable influence of the labels on the migratory aptitude of the components being analyzed. Of particular interest is electrophoresis, such as gel, capillary, etc. Among chromatographic techniques are HPLC, affinity chromatography, thin layer chromatography, paper chromatography, and the like.

The subject labels wherein the polymeric backbone is a nucleic acid chain find particular use as primers in nucleic acid chain extension applications, including sequencing, the polymerase chain reaction, particularly for sizing, or other systems where primers are employed for nucleic acid extension and one wishes to distinguish between various components of the mixture as related to the particular labels.

In sequencing, universal primers may be employed, where a different pair of fluorophores are used for each of the different dideoxynucleosides used for the extension during sequencing. In other words, universal primers may be prepared, where the primer may be any one of the universal primers, having been modified by bonding of the two fluorophores to the primer. Thus, various commercial primers are available, such as primers from pUC/M13, λgt10, λgt11, and the like. See, Sambrook et al., *Molecular Cloning: A Laboratory Manual,* 2nd ed., CSHL, 1989, Section 13. DNA sequences are cloned in an appropriate vector having a primer sequence joined to the sequence to be sequenced. Different 2', 3' ddNTPs are employed, so that termination occurs at different sites, depending upon the particular ddNTP which is present in the chain extension. By employing the subject primers, each ddNTP will be associated with a particular label. After extension with the Klenow fragment, the resulting fragments may then be separated in a single lane by electrophoresis or in a single capillary by electrophoresis, where one can detect the terminating nucleotide by virtue of the fluorescence of the label.

With PCR, where different primers have been used in PCR, each of the primers may be labeled in accordance with the subject invention, so that one can readily detect the presence of the target sequence complementary to each of the different primers. For example, the subject labels may used with the rapid sizing of alleles, as exemplified by short tandem repeat (STR) alleles, or other sequences where one wishes to detect small base or base pair differences, such as small differences of as few as a single base or base pair. By using the subject labels in conjunction with capillary electrophoresis, particularly capillary array electrophoresis, and employing an intercalating agent in the buffer, separations differing by one base may be achieved. The method can be used with dsDNA, particularly dsDNA obtained using the polymerase chain reaction or the ligase chain reaction, where the subject labels may be used as primers. One or both of the primers for the amplification may be labels, where the fluorophore pairs may be the same or different, depending on the needs of the separation. The intercalating agents may be fluorescent or non-fluorescent, such as thiazole orange, 9-aminoacridine, ethidium bromide, and the like, but for the specific example give here they are preferably non-fluorescent. Concentrations will generally be in the range of 0.1 to 10 µM. Conventional conditions may be used for the capillary electrophoresis, using a polyacrylamide wall coating and, for example, using hydroxyethylcellulose at from about 0.5 to 1% in an appropriate running buffer. Voltages may vary from about 50 to 150V/cm or larger. The amount of DNA will generally be in the range of about 1 pg/µl to 1 ng/µl, although greater or lesser amounts may be used. Obviously, such method can also be used for single strand (ss) DNA fragment analysis to detect the labeled ssDNA fragments by virtue of their fluorescence, using linear polyacrylamide or the like in CE, which permits single base resolution.

The subject labels also find use with non-denaturing separation matrices to analyze ds-DNA PCR fragments and STR's, where the use of the subject labels overcomes the disadvantages of nondenaturing separation matrices in such applications, including problems with: single base-pair resolution, the identification of single base insertion/deletion variants, the appearance of extra peaks due to the formation of heteroduplex structures which leads to difficulties in interpretation and multiplexing, and the like. For example, accurate multiplexed STR sizing is routinely achieved using non-denaturing, replaceable sieving matrices and an M13 A-termination ladder as the standard by employing multiplexed STR samples that are amplified with the subject labels, where the subject labels are detected in the green channel and the M13 A-extension produced with a label according to the subject invention is detected in the red channel. The use of the subject labels in such applications provides for separations that are as fast as those achieved under native conditions, with single base resolution and an absence of interference from heteroduplex structures.

Kits are provided having combinations of labels, usually at least 2. Each of the labels will have the acceptor-donor pair, usually with comparable backbones, where the labels will be separated along the backbone to give comparable mobility in the separation method to be used. Each of the labels in a group to be used together will absorb at about the same wavelength and emit at different wavelengths. Each of the labels in the group will have about the same effect on mobility in the separation method, as a result of the variation in placement of the different fluorophores along the backbone.

The kits will generally have up to about 6, usually about up to about 4 different labels which are matching, but may have 2 or more sets of matching labels, having 2–6 different labels.

Of particular interest are labels comprising a nucleic acid backbone, where the labels may be present on the nucleotides which hybridize to the complementary sequence or may be separated from those nucleotides. The entire nucleic acid sequence may be complementary to the 5' primer sequence or may be complementary only to the 3' portion of the sequence. Usually, there will be at least about 5 nucleotides, more usually at least about 8 nucleotides which are complementary to the sequence to be copied. The primers are combined with the sequence to be copied in the appropriate plasmid having the primer sequence at the 3' end of the strand to be copied and dNTPs added with a small amount of the appropriate ddNTP. After extension, the DNA may be isolated and transferred to a gel or capillary for separation.

The kits which are employed will have at least two of the subject labels, which will be matched by having substantially the same absorption for the donor molecule, distinct emission spectra and substantially the same mobility. Generally for single stranded nucleic acids, the separation will be from about 1–15, more usually 1–12, preferably about 2–10 nucleosides between fluorophores.

The following examples are offered by way of illustration and not by way of limitation.

EXPERIMENTAL

I. Preparation of Energy Transfer Fluorescent Dye Labels

A. Design and Synthesis of Energy Transfer Fluorescent Dye Tagged Oligonucleotide Labels Deoxyoligonucleotides (12-base long) with the sequence 5'-GTTTTCCCAGTC-3', (SEQ ID NO:1) selected from the M13 universal primer, were synthesized with donor-acceptor fluorophore pairs separated by different distances. Specifically, the 12-mer contains a modified base introduced by the use of 5'dimethoxytrityl-5-[N-(trifluoroacetylaminohexy)-3-acrylimido]-2'-deoxyUridine, 3'-[(2-cyanoethyl)-(N,N-diisopropyl)]-phosphoramidite (Amino-Modifier C6 dT) (Structure 1), which has a primary amine linker arm at the C-5 position.

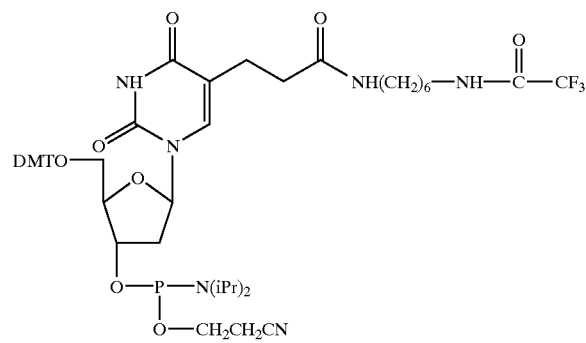

Structure 1. Amino-Modifier C6 dT

The donor dye was attached to the 5' side of the oligomer, and the acceptor dye was attached to the primary amine group on the modified T. The distances between the donor and acceptor were changed by varying the position of the modified T on the oligomer. The primers are denoted as D-N-A, where D is the donor, A is the acceptor and N is the number of bases between D and A. In all the primers prepared, D is Applied Biosystems Inc. ("ABI") dye FAM, a fluorescein derivative, A is ABI dyes TAM or ROX which are both rhodamine derivatives, or JOE, a fluorescein deriva tive. As a representative example, the structure of FAM-3-TAM is shown below (Structure 2).

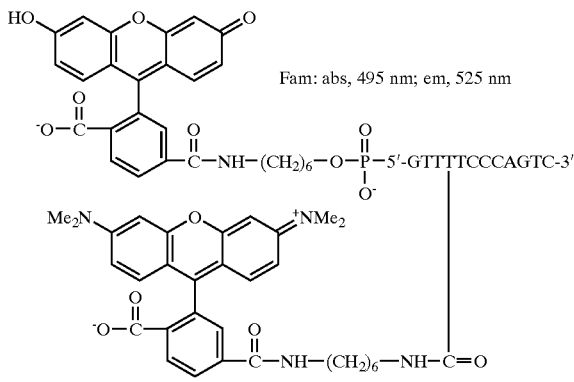

Fam: abs, 495 nm; em, 525 nm

Structure 2. FAM-3-TAM

Figure 2:
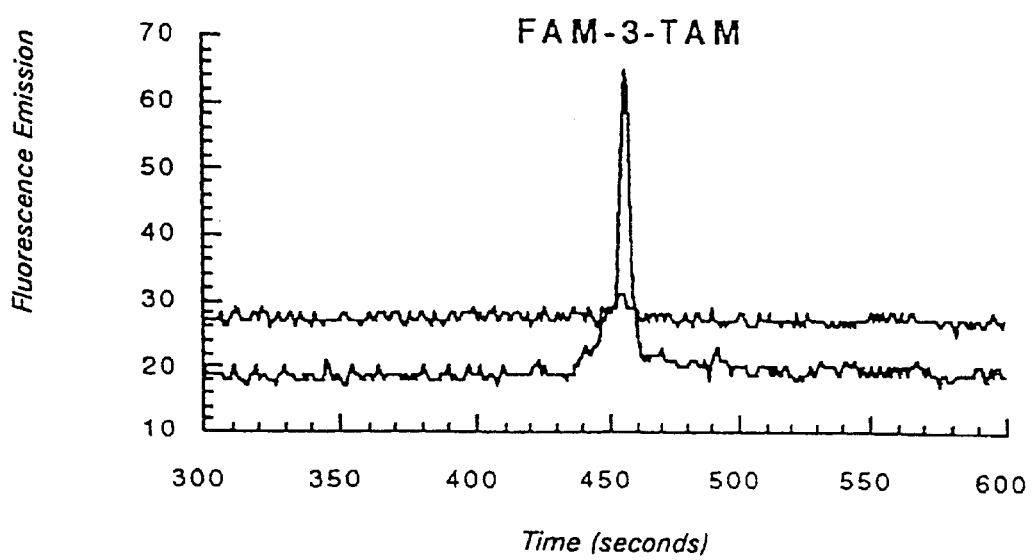
FIG. 2 is a CE electropherogram of FAM-3-TAM. The sample was analyzed by typical capillary electrophoresis DNA sequencing conditions with 488 nm excitation. The green trace is the fluorescence signal detected in the green channel (525 nm), and the red trace is the fluorescence signal detected in the red channel (590 nm). Both channels are detected simultaneously.
Figure 3:
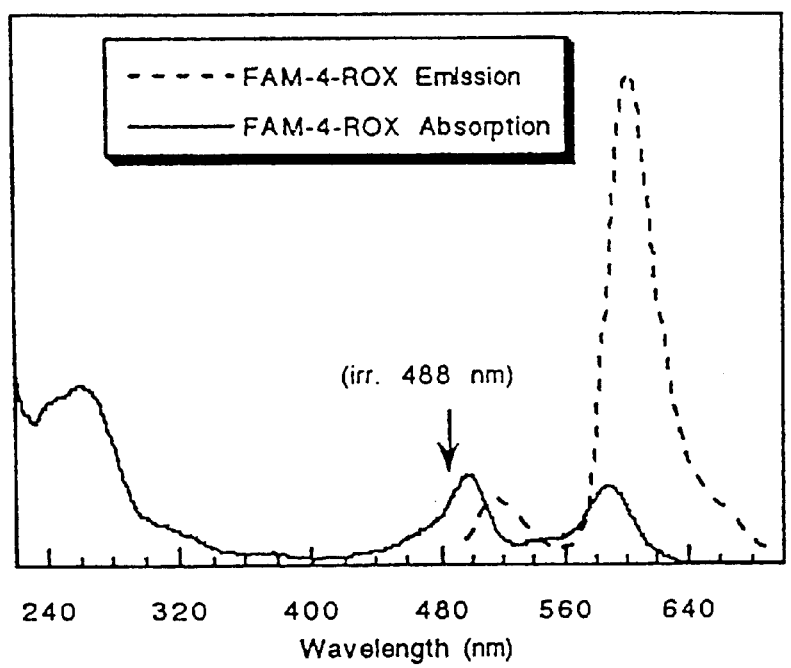
FIG. 3 is a graph of the absorption and emission spectra of FAM-4-ROX in 1×TBE.
Figure 4:
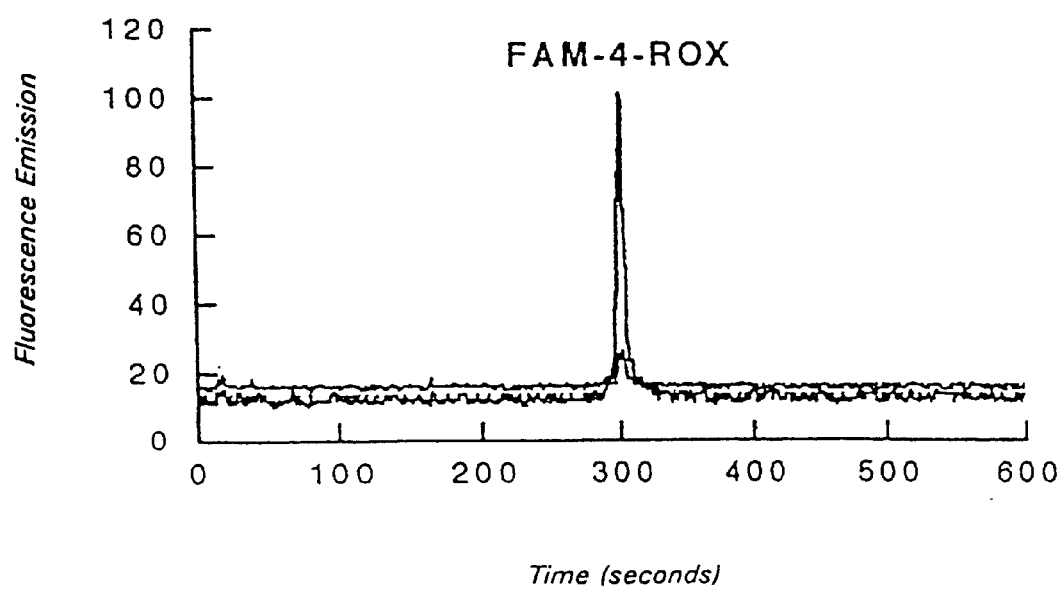
FIG. 4 is a CE electropherogram of FAM-4-ROX. The sample was analyzed by typical capillary electrophoresis DNA sequencing conditions with 488 nm excitation. The green trace is the fluorescence signal detected in the green channel (525 nm), and the red trace is the fluorescence signal detected in the red channel (590 nm). Both channels are detected simultaneously.
Figure 5:
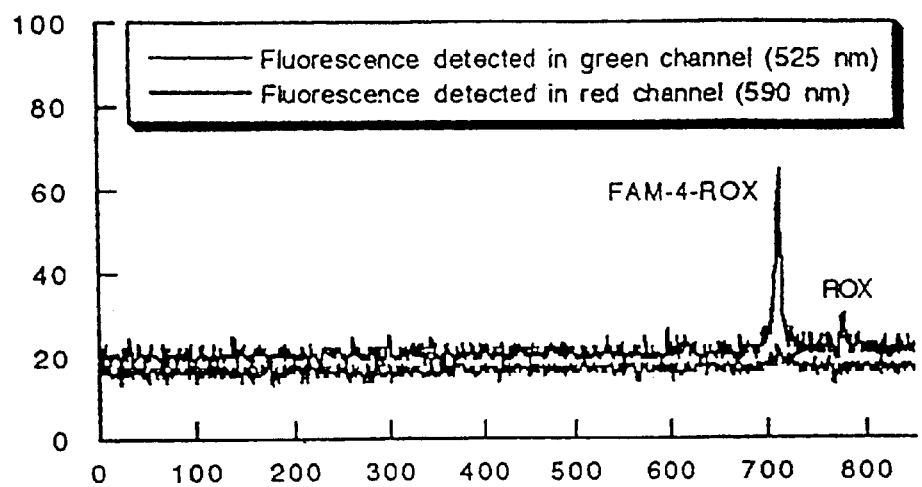
FIG. 5 is a CE electropherogram of FAM-4-ROX and ROX primer. The two primers at the same concentration were mixed together in 80% formamide and injected into the capillary. The fluorescence signals were detected in the green and red channels simultaneously with 476 nm excitation.

The advantages of the energy transfer approach described here are (1) that a large Stokes shift and much stronger fluorescence signals can be generated when exciting at 488 nm and (2) that the mobility of the primers can be tuned by varying the distances between the donor and acceptor to achieve the same mobility. The visible spectrum of FAM-3-TAM has both the absorption of FAM (495 nm) and TAM (560 nm); however with excitation at 488 nm nearly all of the emission comes out from T with a maximum at 579 nm (FIG. 1). This demonstrates efficient fluorescence energy transfer from FAM to TAM. This can also be seen by running the primer down a capillary electrophoresis (CE) column and detecting in red and green channels. With a FAM- and TAM-labeled primer, nearly all the emission is seen in the red channel (590 nm) (FIG. 2), indicating that the energy from donor FAM was transferred almost completely to the acceptor TAM, producing a Stokes shift of 91 nm. The observation of a single peak indicates the primer is pure. The same outcome is seen for FAM-4-ROX, which gives even a larger Stokes shift of 114 nm (FIGS. 3 and 4). Enhancement of the fluorescence signals of the energy transfer primers compared to single dye labeled primer is seen, where an ABI ROX primer at the same concentration as that of FAM-4-ROX (measured by UV) was injected in the same capillary. The resulting fluorescence signal of FAM-4-ROX is seen to be more than ten times higher than that of the ROX primer (FIG. 5).

Figure 6:
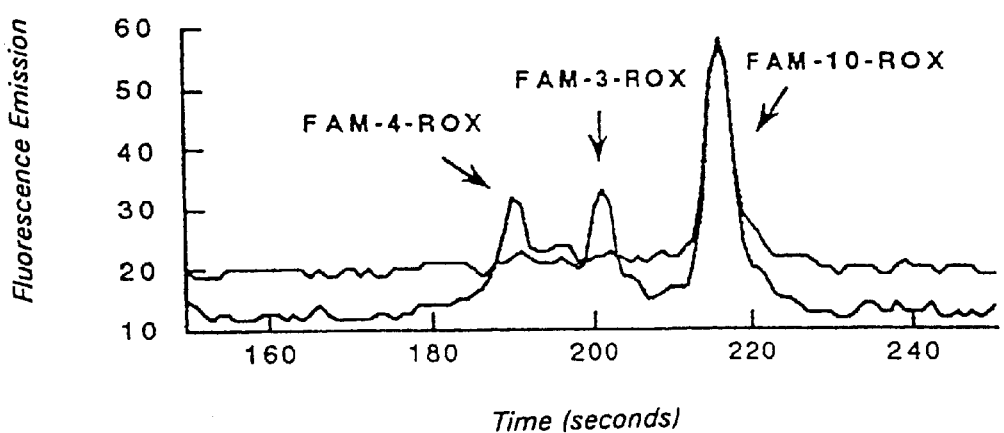
FIG. 6 is a CE electropherogram of a FAM-3-ROX, FAM-4-ROX and FAM-10-ROX mixture, showing the dependence of the mobility on the distance between the donor and acceptor. The sample was analyzed by typical capillary electrophoresis DNA sequencing conditions with 488 nm excitation; and emission at 525 nm (green channel) and 590 nm (red channel).

For the successful application of donor-acceptor fluorophore labeled primers to DNA sequencing, it is advantageous that the primers produce the same mobility shifts of the DNA fragments and display distinct fluorescence signals. It was found that the mobility of the primers depends on the distance between the donor and acceptor (FIG. 6). FAM-4-ROX, FAM-3-ROX and FAM-10-ROX were separated on a capillary and detected in red and green channels. For FAM-10-ROX the increased distance between the dyes reduces the amount of energy transfer, resulting in almost equal signals in the two channels. As the separation distance is reduced, the amount of energy transfer increases as evidenced by the reduced relative green signal. FAM-3-ROX and FAM-4-ROX both exhibit excellent energy transfer, but their mobilities are distinctly different, which offers the potential of tuning the mobility shift by varying the distance. To get an exact match of the mobility of two primers that have distinctly different emission spectra, FAM-3-FAM, FAM4-FAM and FAM-10-FAM were also prepared.

Figure 7:
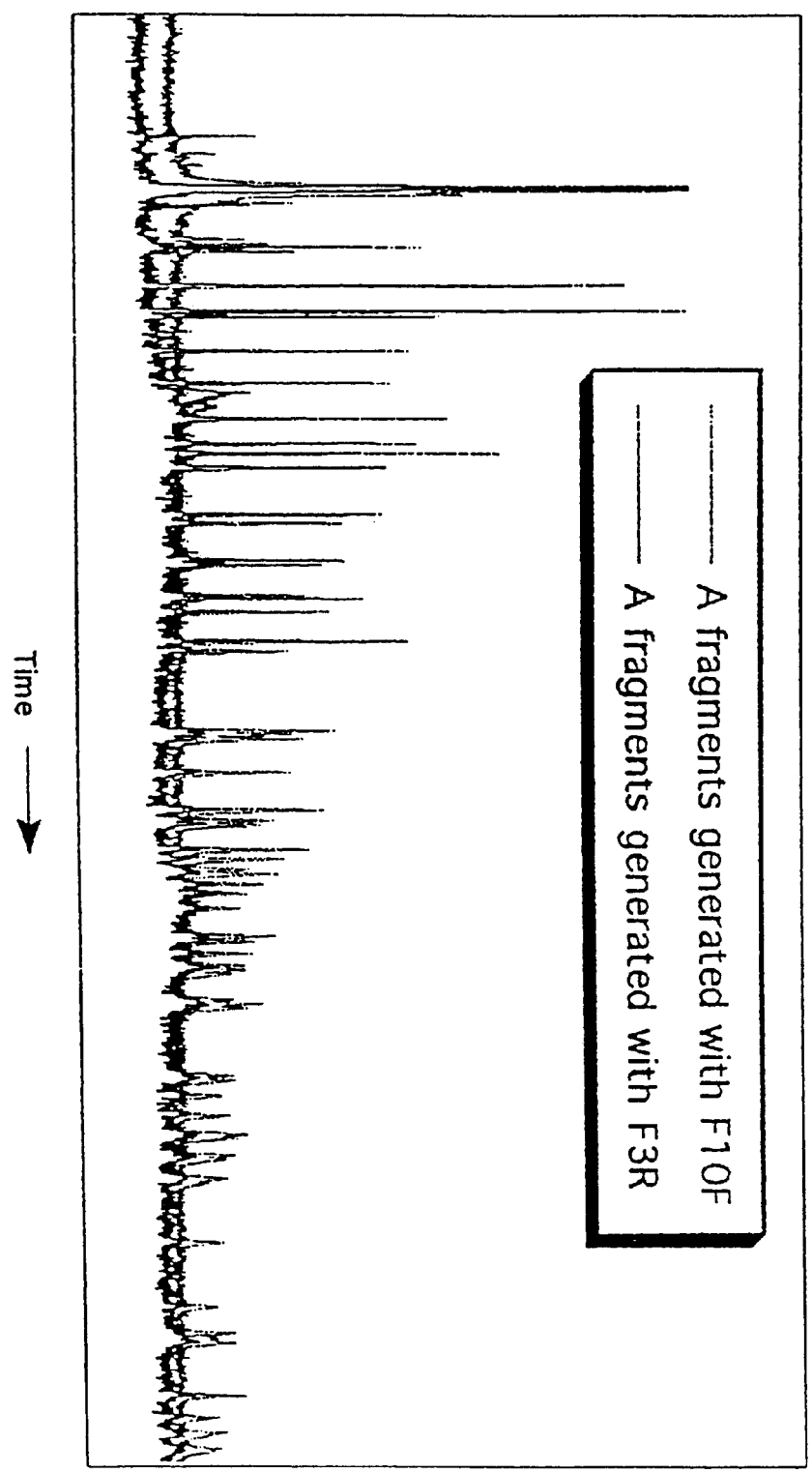
FIG. 7 is a comparison of the mobility shift of different dye primers on M13 mp 18 A fragment DNA samples.

Among a library of primers prepared (FAM-N-FAM, FAM-N-TAM, FAM-N-ROX), it was found that sequencing fragments terminating in A, generated with FAM-10-FAM and FAM-3-ROX using Sequenase 2, have very similar mobility shifts (FIG. 7), demonstrating the potential for DNA sequence analysis. The emission of FAM-10-FAM and FAM-3-ROX are at 525 nm and 605 nm respectively.

B. Preparation of 12-mer Oligonucleotides Containing a Modified T and a FAM Label at the 5' Position.

The following three primers were prepared on an ABI Model 394 DNA synthesizer in a 0.2 μmol scale:

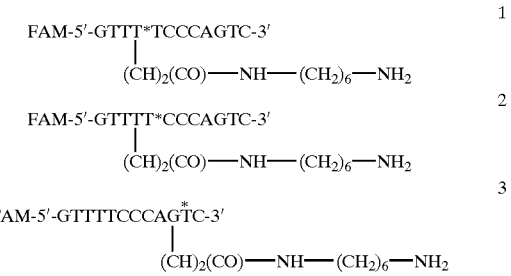

The modified base T* containing an amino linker arm was introduced to the defined position by using Amino-Modifier C6 dT phosphoramidite (Glen Research) and FAM was introduced by using 6-FAM amidite (ABI) in the last step of the synthesis. After the base sequences were completed, the oligonucleotides were cleaved from the solid support (CPG) with 1 ml concentrated $NH_4OH$. The amino protecting groups on the bases (A, G, C and T*) were removed by heating the $NH_4OH$ solution for 4 hours at 55° C. Capillary electrophoresis analysis indicated that the oligomers were ~80% pure, and they were used directly in the next dye-coupling step.

C. Attachment of the Second Fluorescent Dye to the Amino Linker Arm of the Oligomers 1, 2 and 3

As a representative example, the reaction scheme to couple the second dye (TAM) to the oligomer 1 is shown below:

The FAM-labeled oligonucleotides (1, 2 and 3) in 40 μL 0.5 M $Na_2CO_3$/$NaHCO_3$ buffer were incubated overnight at room temperature with approximately 150 fold excess of either TAM-NHS ester, ROX-NHS ester or FAM-NHS ester in 12 μL DMSO. Unreacted dye was removed by size exclusion chromatography on a Sephadex G-25 column. The two dye labeled oligonucleotides were then purified by 6 M urea-TBE, 20% acrylamide gel electrophoresis (40 cm×0.8 cm). The pure primers were recovered from the gel and desalted with Oligonucleotide Purification Cartridge (Applied Biosystems, Foster City, Calif.). The purity of the primers was shown to be >99% by capillary gel electrophoresis.

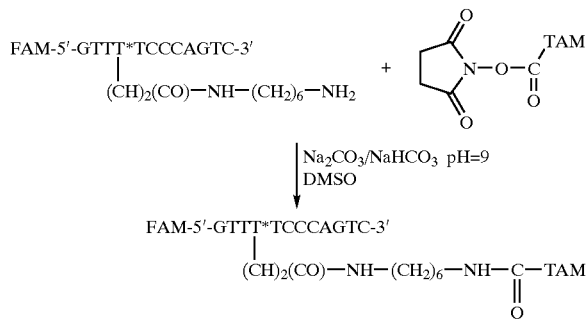

D. Preparation of Additional Energy Transfer Labels

To prepare the ET primers, the donor FAM was introduced by using 6-FAM amidite in the last step of the oligonucleotide synthesis on a DNA synthesizer. After cleavage from the solid support and removal of the base protecting groups, the primers were evaporated to dryness under vacuum (0.5 mm Hg). To incorporate the acceptor dyes, 15–20 nmol of FAM-labeled T*-containing oligonucleotides in 40 μl 0.5 M $Na_2CO_3$/NaHCO (pH 9.0) buffer were incubated overnight at room temperature with an approximately 150-fold excess of corresponding FAM, JOE, TAMRA and ROX N-hydroxysuccinimidyl esters in 12 μl DMSO. Unreacted dye was removed by size exclusion chromatography on a Sephadex G-25 column (Pharmacia, Piscataway, N.J.). The ET primers were then purified by electrophoresis in a 20% polyacrylamide gel containing 6 M urea (40 cm×0.8 cm). The purified primers were recovered from the gel slices and desalted with Oligonucleotide Purification Cartridge. The single dye-labeled primers with the same sequence as that of the ET primers were prepared by the standard protocol using Aminolink 2 (Applied Biosystems, Foster City, Calif.). The purity of the primers was shown to be >99% by polyacrylamide capillary gel electrophoresis. Primers were quantified by their 260 nm absorbances and then stored in 10 mM Tris-Cl, 1 mM EDTA (pH 8.0) at a final concentration of 0.4 pmol/μl for DNA sequencing reactions.

Figure 8:
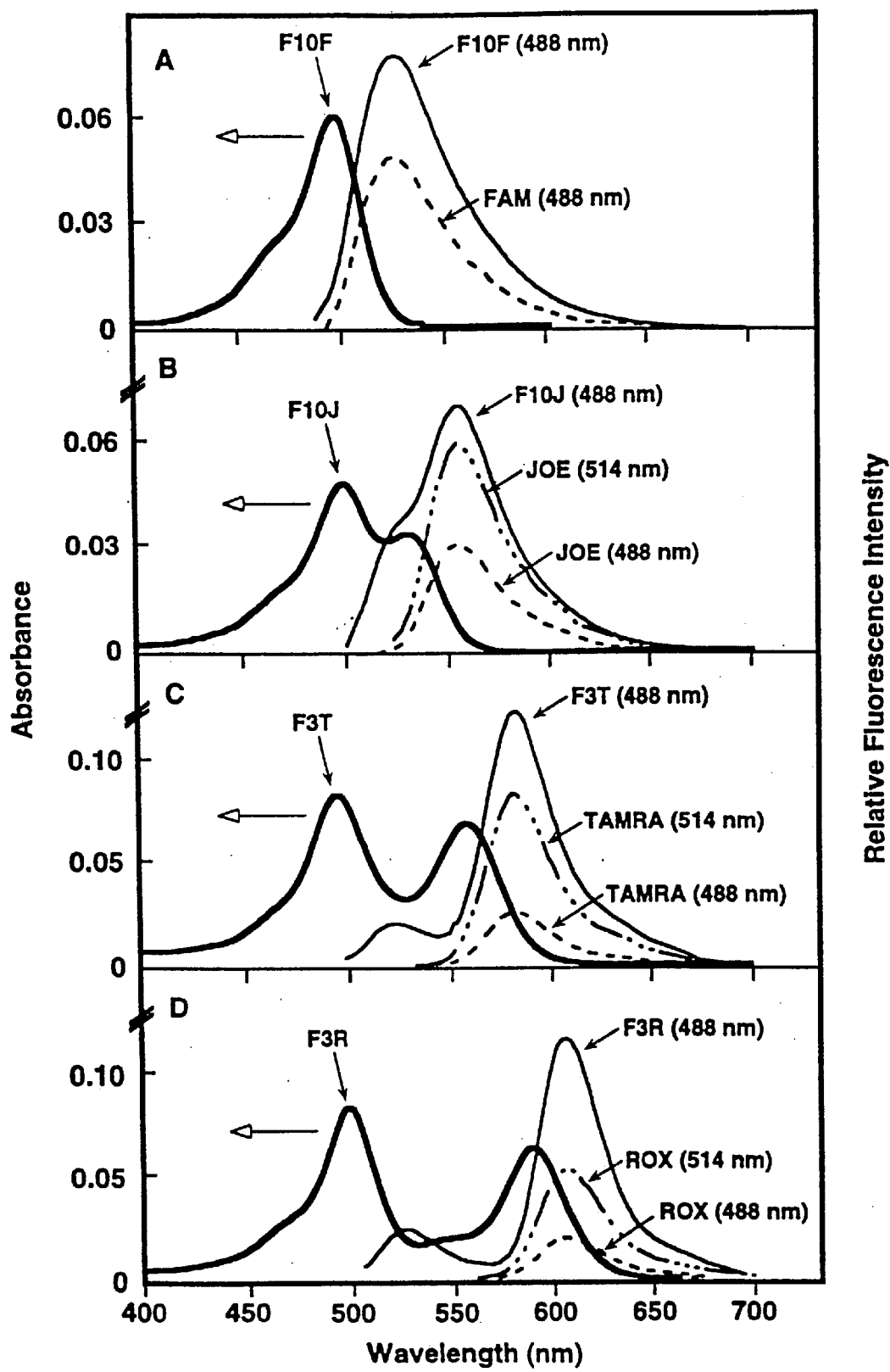
FIG. 8 shows the comparison of the fluorescence emission intensity of the four energy transfer (ET) primers (F10F, F10J, F3T and F3R) with the corresponding single dye-labeled primers at the indicated excitation wavelength (1×TBE, 7 M urea). The thick lines indicate the absorption spectra of the ET primers. (A) F10F vs. FAM, (B) F10J vs. JOE, (C) F3T vs. TAMRA and (D) F3R vs. ROX. The emission spectra for each primer pair were determined using solution having the same molar concentration.
Figure 9:
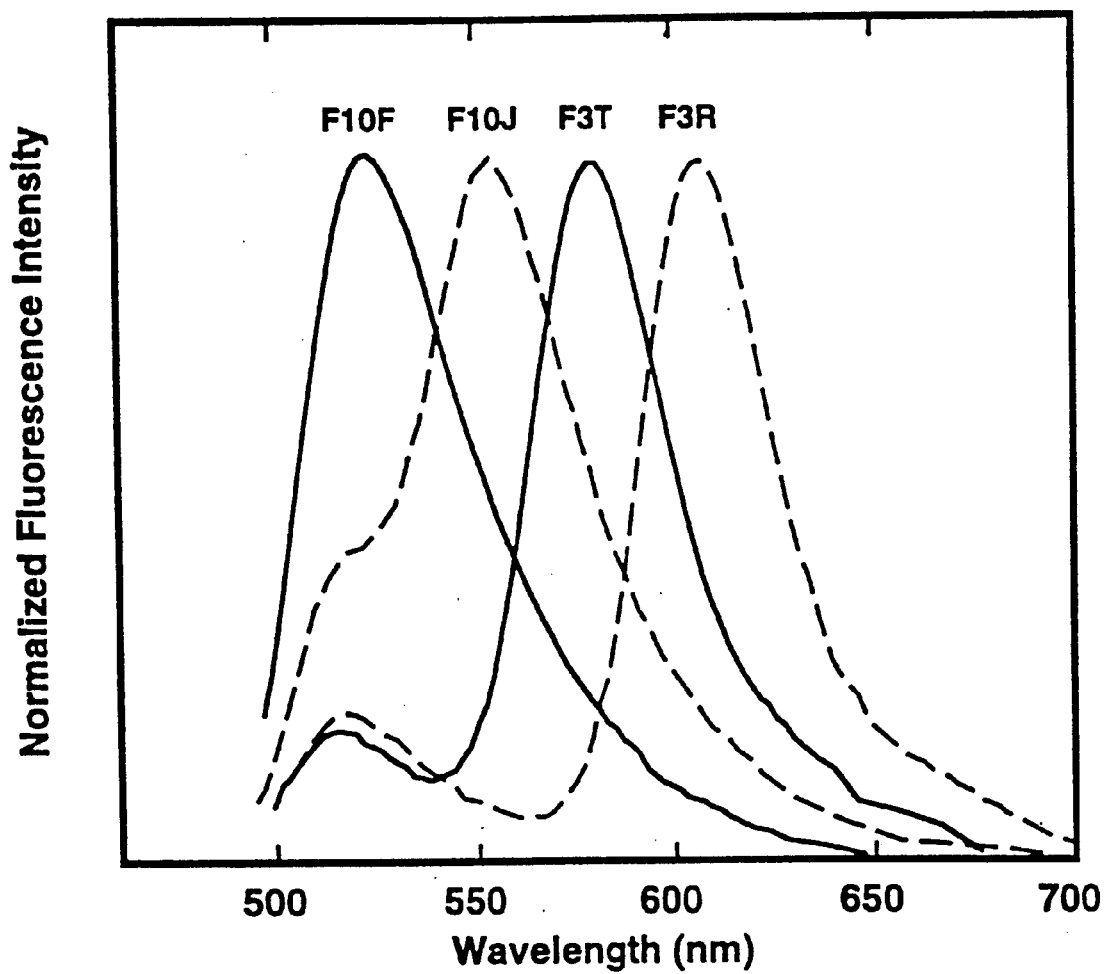
FIG. 9 shows the normalized fluorescence emission spectra of the four ET primers (F10F, F10J, F3T and F3R) (1×TBE, 7 M urea).
Figure 10:
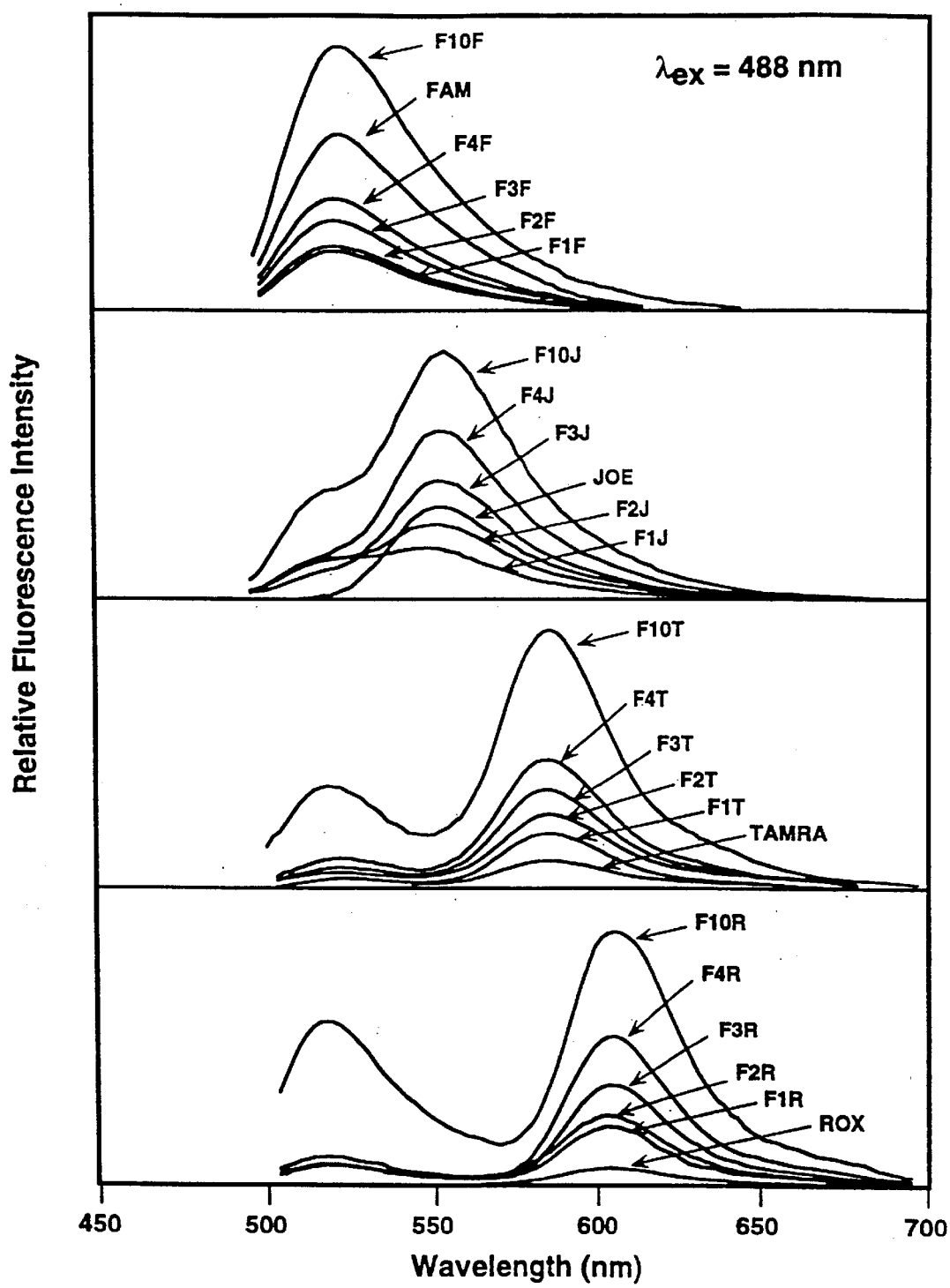
FIG. 10 shows that the fluorescence emission intensity of the ET primers is increased as the distance between the donor and acceptor increases. The emission spectra for each primer series were determined at the same molar concentration in 1×TBE.
Figure 11:
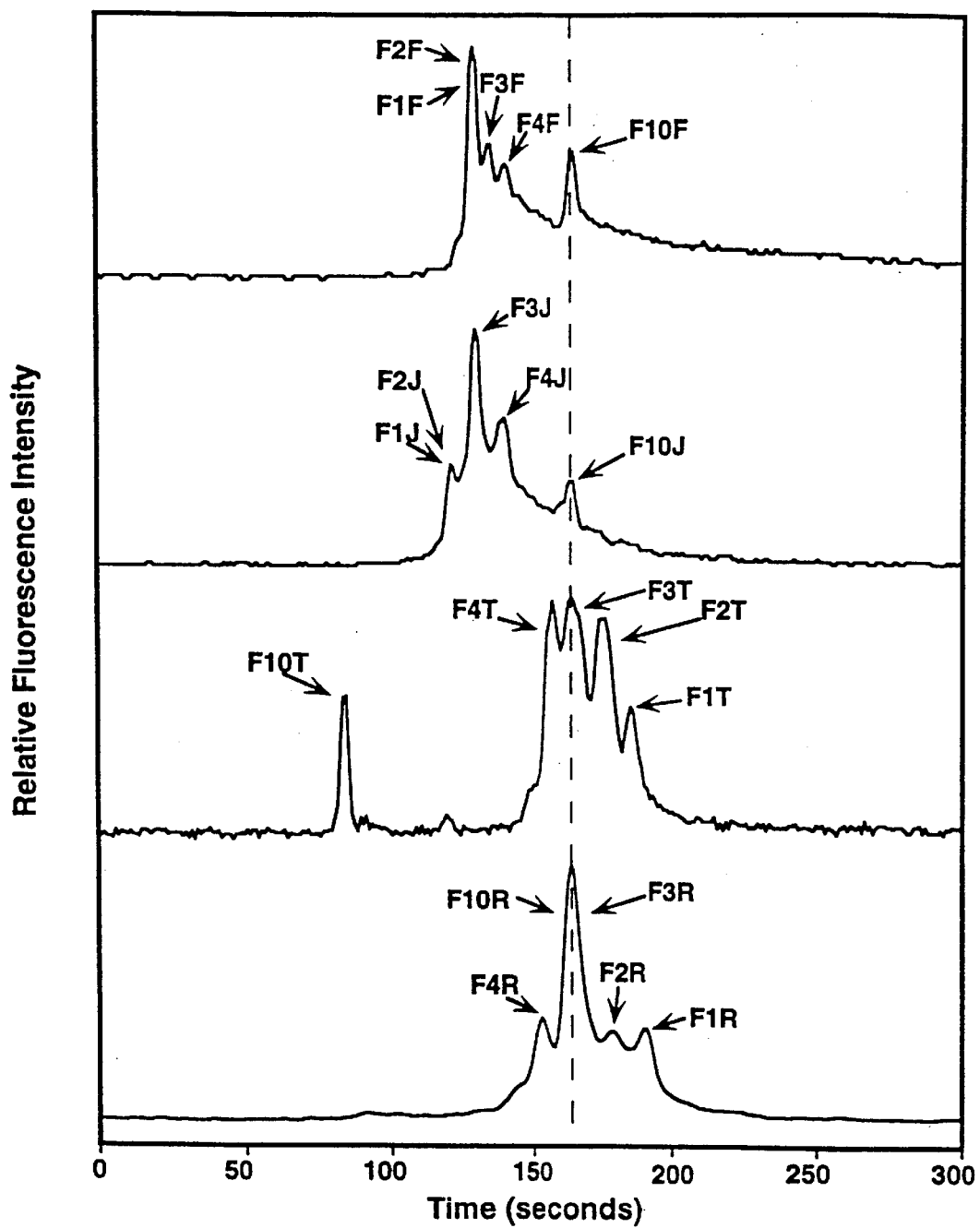
FIG. 11 shows capillary electropherograms of each ET primer series. A separate experiment has established that F10F, F10J, F3T and F3R have very similar mobilities. The mobilities of the other primers are shown for each set, relative to that of F10F, F10J, F3T and F3R, respectively. Sample was analyzed by typical capillary electrophoresis (CE) DNA sequencing conditions with 488 nm excitation.
Figure 12:
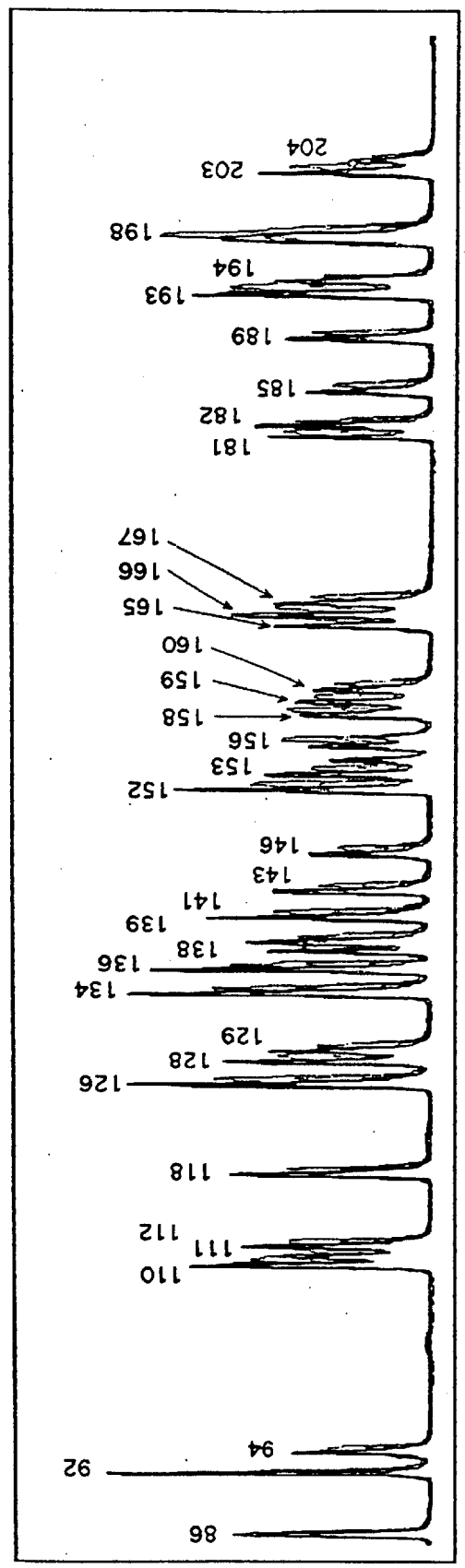
FIG. 12 shows that the mixed single base (ddATP/dNTPs) DNA sequencing fragments generated with F10F, F10J, F10T and F10R individually and then combined together have substantially the same mobility shift. Samples were prepared using Sequenase 2.0 Kit (USB/Amersham LIFE SCIENCE) and run on a 4-color CE DNA sequencer.

Twenty ET primers were synthesized with the same donor at 5' end and different acceptors at different positions on the primer sequence. The spacing between the two chromophores is altered by varying the position of T' in the synthesis of each primer. We found that the electrophoretic mobility of the ET primers depends on the spacing between the donor and acceptor. Within a range of distances determined by the number of intervening bases that allow good energy transfer, it is possible to adjust the electrophoretic mobility of the primers. The advantages of the energy transfer approach described here are (1) that a large Stokes shift and much stronger fluorescence signals can be generated when exciting at 488 nm and (2) that the mobility of the primers can be tuned by varying the distances between the donor and acceptor to achieve the same mobility. As a representative example, FIG. 8 presents the absorption and emission spectra of the ET primer F10F, F10J, F3T and F3R. Each ET primer exhibits the characteristic absorption of FAM at 496 nm as well as strong absorption at 525 nm due to JOE in F10J, at 555 nm due to TAMRA in F3T and at 585 nm due to ROX in F3R. The fluorescence spectra of the ET primers are dominated by the acceptor emissions. While the emission maximum of F10F is at 525 nm, the emission of F10J with 488-nm excitation is Stokes-shifted to 555 nm, that of F3T is shifted to 580 nm, and that of F3R is shifted to 605 nm. In the case of F3R, the Stokes shift is over 100 nm. FIG. 8 also presents emission spectra of the single dye-labeled primers measured at the same molar concentration as that of the corresponding ET primers. Substantial enhancement of the ET primer emission intensity is observed compared to the corresponding single dye-labeled primers, indicating that efficient energy transfer is occurring. The fluorescence intensity improvements derived from FIG. 8 are: F10F=1.8×FAM; F10J=2.5×JOE or 1.4×JOE when JOE is excited at 514 nm; F3T=5.3×TAMRA or 1.7× TAMRA when TAMRA is excited at 514 nm; F3R=6.2× ROX or 2.3×ROX when ROX is excited at 514 nm. Thus, the fluorescence intensity of single JOE, TAMRA and ROX labeled primer with 514 nm excitation is still less than that of the corresponding ET primer with 488 nm excitation. To evaluate the emission spectral purity of the four ET primers, their normalized emission spectra are presented in FIG. 9. It can be seen that the residual emission of FAM in F10J, F3T and F3R is very small. Based on a comparison of the residual FAM emission in the ET primers with that of a FAM-labeled primer with same sequence and length, the energy transfer efficiency was calculated to be 65% for F10J, 96% for F3R and 97% for F3T. FIG. 10 presents the fluorescence intensity comparison of the ET primer series as well as the corresponding single dye-labeled primers measured at the same molar concentration. The results indicate that when the two fluorophores are too close to each other, fluorescence quenching occurs. The fluorescence intensity increases with the increase of the separation distances between the donor and acceptor. Strong fluorescence signals were obtained when the separation distance is 10-bases. The fluorescence intensity of F10T and F10R measured at the acceptor emission region is 10 and 14 times that of TAMRA and ROX primer respectively. Thus, the maximum fluorescence signals can be increased as much as 14-fold using the ET principle. The results also indicate that the donor FAM emission intensity in F10T and F10R is higher than the other ET primers. However, for a particular primer, as long as the acceptor emission is higher than or equal to that of the donor and the net fluorescence signal is intense, it is valuable for DNA analysis. The mobility comparison of ET primers on polyacrylamide capillary electrophoresis are shown in FIG. 11 which indicates that F10F, F10J, F10R, F3T and F3R have very similar mobility shifts. Although F10T has large mobility difference compared to F10F, F10J and F10R, FIG. 12 shows that the extended ddAPT/dNTPs DNA fragments generated with F10T have similar mobilities as those generated with F10F, F10J and F10R. This indicates that as the DNA fragments grow longer than 18 bases, DNA fragments generated with F10T have essentially the same conformation as fragments generated with F10F, F10J and F10R. For the successful application of donor-acceptor fluorophore labeled primers to DNA sequencing, it is useful that the primers produce same mobility shifts of the DNA fragments and display distinct fluorescence signals. Six primers (F10F, F10J, F10T, F10R, F3T and F3R) were therefore selected for evaluation in DNA sequencing.

II. Preparation of STR Samples for Denaturing Gel Analysis

ET primers for PCR were synthesized by the phosphoramidite method on an Applied Biosystems 392 DNA synthesizer. The structures of the blank and energy-transfer dye-labeled PCR primers for VWFA, THO1, TPO, and CSF loci are presented in Scheme III. Primer sequences followed published sequences (THO1 (Edwards et al., Am. J. Hum. Genet. (1991) 49:746–756), TPO (Huang et al., Forensic Science International (1995) 71: 131–136; CSF (Hammond et al., Am. J. Hum. Genet. (1994) 55: 190–195), VWFA-B (Kimpton et al., PCR Methods and Applications (1993) 3:13–22) except VWFA-B which was redesigned to avoid hairpins and dimer formation; as a result, VWFA products are 5 bp longer than those reported by Kimpton (1993). The energy-transfer dye-labeled primers are advantageous for two-color fragment sizing because the 488-nm exciting light is optimally absorbed by the FAM chromophore in these primers followed by enhanced emission at the FAM wavelength for the THO1 locus (amplified with F6F) and for the VWFA, TPO and CSF loci (amplified with F8F primers), or very distinctively Stokes-shifted emission following energy transfer in the case of the M13 A-termination ladder (generated with the F10R primer (Wang et al., Anal. Chem. (1995) 67:1197–1203 and Ju et al., Anal. Biochem. (1995) 231: 131–140). Primers were dissolved in 10 mM Tris-HCl, 1 mM EDTA buffer at a final concentration of 10 $\mu$M for PCR reactions and 0.4 $\mu$M for the M13 sequencing reaction.

For PCR amplification of multiplexed STR loci, DNA was isolated from blood using standard methods (Sambrook, J., Fritsch, E. F., Maniatis, T., Molecular Cloning: A Laboratory Manual, (2nd ed. Cold Spring Harbor Laboratory, Cold Spring Harbor, N.Y.)(1989)). PCR multiplex amplifications for VWFA, THO1, TPO, and CSF loci were performed in 25 $\mu$l volumes using 10 ng genomic DNA template, 0.5 $\mu$M of each forward fluorescent and reverse blank primers for VWFA, THO1 TPO and CSF loci, 2.5 units of Taq DNA polymerase, 50 mM KCL, 1.5 mM MgCl$_2$, 10 mM Tris-HCL at pH 8.3 and 200 $\mu$M dNTPs (final concentrations indicated). The PCR cycle protocol using a Perkin Elmer Cetus Model 480 was: (1) melting at 95° C. for 3 min, (2) 28 cycles at 95° C. for 1 min. then 59° C. for 1 min, then 72° C. for 1 min, (3) 72° C. for 2 min to complete extension. The locus types for all samples used in this study were independently determined by analysis on slab gels essentially as described by Puers et al., Am. J. Hum. Genet. (1993) 53:953–958, with SybrGreen staining and detection on a Molecular Dynamics FluorImager 575.

III. Sequencing Applications with Energy Transfer Primers

Figure 13:
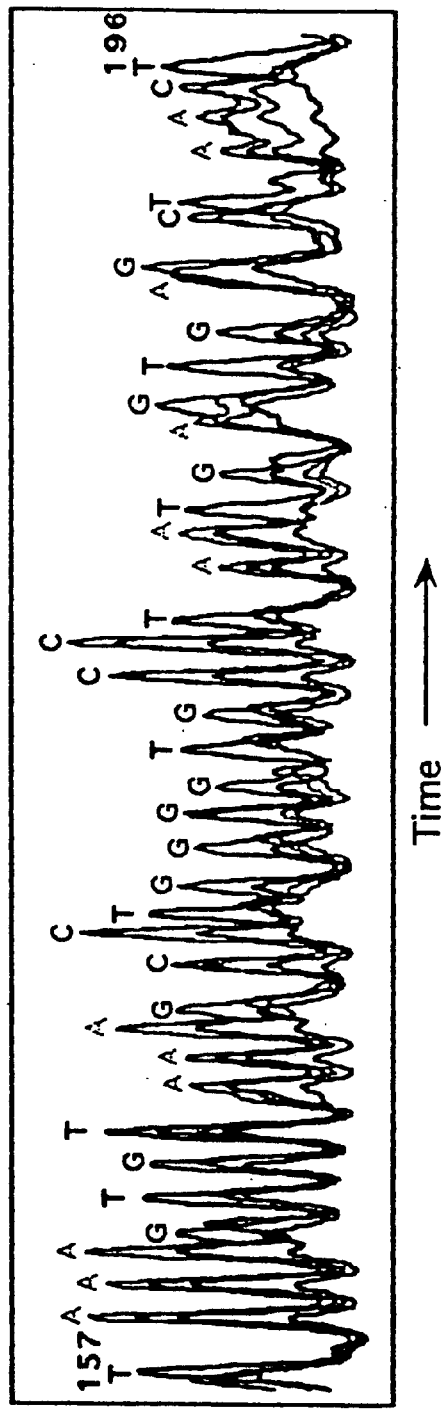
FIG. 13 shows a portion of 4-color raw data (base 157 to 196) of DNA sequencing profile of M13mp 18 DNA using the ET primer F10F, F10J, F10T and F10R and Sequenase 2.0. Primer concentration: 0.4 pmol; DNA template: 0.8 $\mu$g (0.2 $\mu$g for each base extension).

DNA sequencing using primers F10F, F10J, F10T and F10R on CE sequencer was performed using 0.4 pmol of primer and 0.2 $\mu$g of template DNA for each base extension. The sequences extended to more than 600 bases, a portion of which (raw data) is shown in FIG. 13. From this raw data, sequences can be determined by the color on the top peak of the electropherograms. This is the first 4-color sequencing plot without any mobility shift adjustment.

Figure 14:
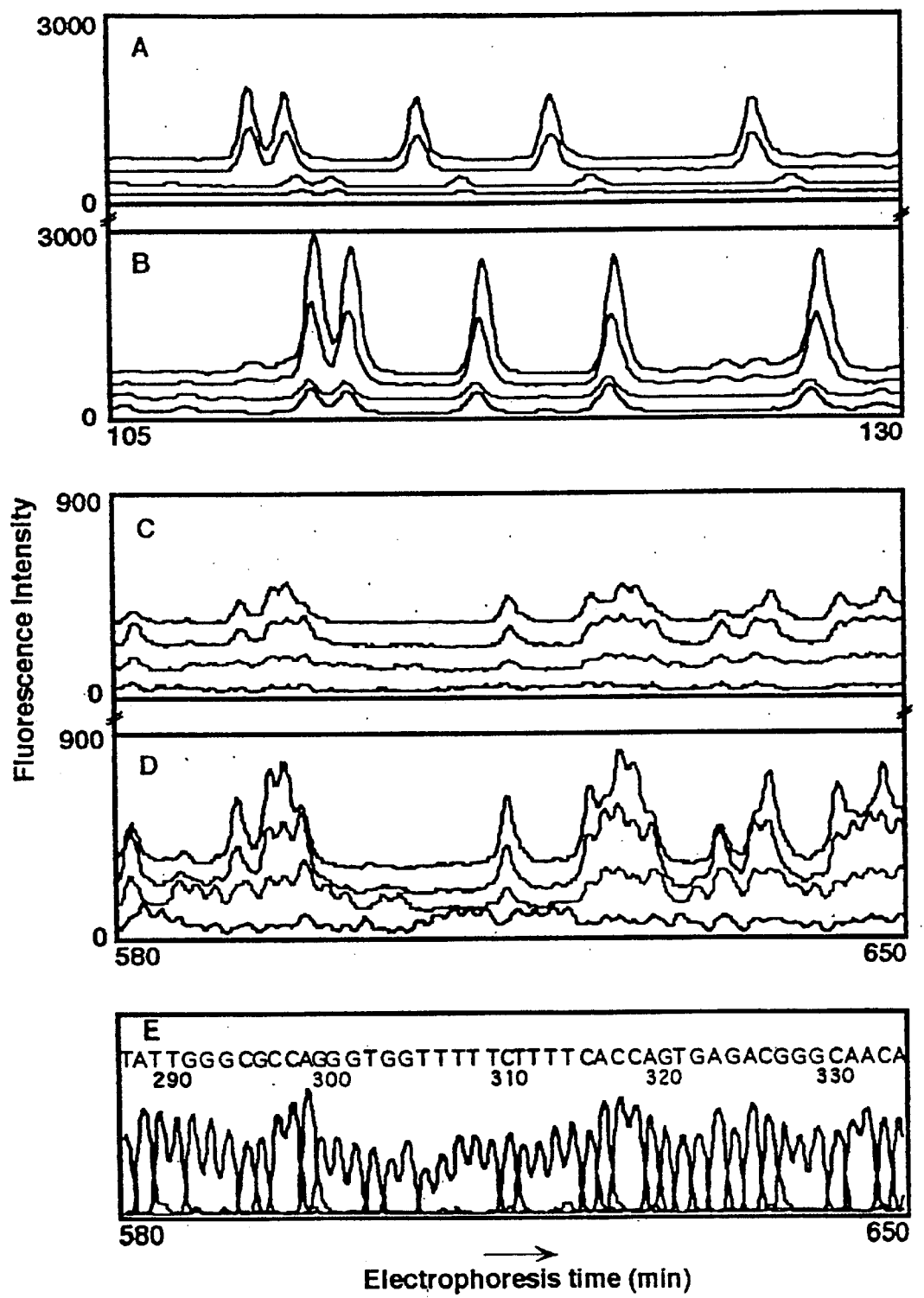
FIG. 14 shows the comparison of signal strengths and mobility shifts of the single dye-labeled primers and ET primers. A total of eight sequencing reactions with ddTTP/dNTPs were run using 1 $\mu$g of M13mp18 DNA template and 0.4 pmol of primer and then loaded in 8 adjacent lanes of the ABI 373A sequencing gel. Panel A shows the raw traces obtained when single dye-labeled primers were used. Colors correspond to the dye as follows: blue, FAM; green, JOE; black, TAMRA; red, ROX. The region shown corresponds to the sequence approximately 15–35 bases from the 3' end of the primer. Panel B shows raw traces on identical scales obtained using ET primers. Colors correspond to the dye as follows: blue, F10F; green, F10J; black, F3T; red, F3R. Panels C and D display data from 4-color sequencing reactions run with single-dye primers (C) and ET primers (D) on identical scales. For reference, the ET primer data in (D) is also shown in analyzed format in panel E. The reactions used for panel C included 0.4 pmol of FAM and JOE primer; 0.8 pmol of TAMRA and ROX primer, and the reactions for panel D and E included 0.4 pmol of each ET primer and a total of 6 $\mu$g of M13mp18 template DNA.

ET primers described here also provide better results and higher sensitivity on the commercial 4-color DNA sequencer. To demonstrate the advantage of ET primers versus conventional single-dye labeled printers. DNA sequencing samples generated with primer F10F, F3T and F3R were analyzed on an Applied Biosystems 373A sequencer. Single base extension (ddTTP/dNTPs) experiments were performed to examine the relative mobility shift and sensitivity of DNA fragments generated with the ET primers. FIG. 14 presents raw fluorescence intensity traces from electrophoresis run on an ABI 373A sequencer. The graphs in FIG. 14A were obtained using M13 (−40) primers labeled with single dye molecules. The differences in electrophoretic mobility of the DNA fragments can be clearly seen. The TAMRA- and ROX-labeled fragments migrate about one base slower than the FAM- and JOE-tagged DNA fragments and have dramatically weaker fluorescence intensities. The corresponding runs with the ET primers are presented in FIG. 14B. The mobilities of the DNA fragments are more closely matched (less than a quarter of a base difference).

To further quantify the instrument sensitivity with the ET primers under slab gel conditions, reactions were run using a constant amount of primer (0.4 pmol) and varying the amount of M13mp18 template DNA (0.05–1 pmol). Graphs of several band intensities against quantity of template were made. This method indicates that the sensitivity for the F10F primer is 160% that of the FAM primer. Similarly, the sensitivity for the F10J, F3T and F3R primers is 360%, 400% and 470% that of JOE, TAMRA and ROX primers, respectively. In experiments which included an excess of template DNA over primer, only a small fraction of either ET or single-dye labeled primer remained unextended. Thus, no significant difference was seen in the efficiency with which the ET primers were extended by polymerase compared with single-dye labeled primers.

Typical raw fluorescence intensity traces for 4-dye, single lane sequences are presented in FIGS. 14C and 14D. Shown here is a portion from the middle of the run spanning about 45 bases. On this intensity scale, the peaks from the red filter are barely discernible when single ROX-labeled primer is used (C). In contrast, all of the sequence-dependent intensity fluctuations are readily seen with the ET primers in the raw data (D). While four-color sequences run with this instrument typically require 3-fold more template and 2-fold more primer in the reactions containing TAMRA- and ROX-labeled primers, the four reactions used for FIG. 14D contained equal amounts of ET primer and template. This change in reaction balance was made possible by the increased relative intensities of the F3T and F3R primers. With these four primers, DNA sequencing on M13Mp18 template produces 510 bases with accuracy of over 99.8%. This sequence can be obtained using a total of 0.6 $\mu$g (0.24 pmol) of M13 template DNA which is approximately one-fourth the amount of template DNA required to give similar sequence accuracy with single dye-labeled primers.

IV. Polymerase Chain Reaction Applications Employing ET Primers

A. Rapid Sizing of Short Tandem Repeat (STR) Alleles Using Energy-Transfer (ET) Fluorescent Primers and Capillary Array Electrophoresis 1. Instrumentation Capillary array electrophoresis separations were detected with the laser-excited, confocal-fluorescence scanner as previously described by Huang et al.(Huang et al. (1992) Anal. Chem. 1992, 64, 967–972. and Anal. Chem. 1992, 64, 2149–2154). Briefly, excitation light at 488 nm from an argon ion laser is reflected by a long-pass dichroic beam splitter, passed through a 32x, N.A. 0.4 microscope objective, and brought to a 10 $\mu$m diameter focus within the 75 $\mu$m i.d. capillaries in the capillary array. The fluorescence is collected by the objective, passed back through the first beam splitter to a second dichroic beam splitter that separates the red ($\lambda$>565 nm) and green ($\lambda$<565 nm) detection channels. The emission is then focused on 400 $\mu$m diameter confocal pinholes, spectrally filtered by a 590 nm long-pass filter (red channel) or a 20 nm band-pass filter centered at 520 nm (green channel), followed by photomultiplier detection. The output is preamplified, filtered, digitized, and then stored in an IBM PS/2 computer. A computer-controlled stage is used to translate the capillary array past the optical system at 20 mm/s. The fluorescence is sampled unidirectionally at 1500 Hz/channel. The scanner construction and operation have recently been described in detail (Mathies et al. (1994), Rev. Sci. Instrum. 65, 807–812). Postacquisition image processing was performed with the programs IPLab, KaleidaGraph and Canvas.

2. Capillary Electrophoresis

Polyacrylamide-coated, fused-silica capillaries were prepared using a modification of the procedure described by Hjertén et al. ((1985), J. Chromatogr. 347, 191–198). A 2–3 mm wide detection window was produced by burning off the polyimide coating with a hot wire followed by cleaning the external surface with ethanol. The detection window was placed 25 cm from the injection ends of the 75 µm i.d., 350 µm o.d., 50 cm long fused silica capillaries (Polymicro Technologies, Phoenix, Ariz.). The inner walls of the capillaries were incubated with 1 N NaOH for 30 min at room temperature, followed by rinsing with deionized water. The capillaries were then treated overnight at room temperature with γ-methacryloxypropyl-trimethoxysilane (1: 250 dilution with $H_2O$ adjusted to pH 3.5 with acetic acid) to derivatize the walls for acrylamide binding. Freshly-made 4% T acrylamide solution in ½×TBE buffer (45 mM tris, 45 mM boric acid, 1 mM EDTA, pH 8.3) was filtered with a 0.2 µm syringe filter and degassed under vacuum for 30 min. One µl TEMED (tetramethylethylenediamine) and 10 µl of 10% APS (ammonium persulfate) solution were added to 1 ml of gel solution. The solution was immediately forced into the capillary with a 100-µl syringe. After 30 min, the acrylamide solution was flushed out with deionized water and capillaries were filled with buffer consisting of hydroxyethyl cellulose (HEC) ($M_n$=438,000, Aqualon Co. Hopewell, Va.) dissolved in ½×TBE. The separation buffer was prepared by adding 0.8 g HEC to 100 ml ½×TBE and dissolved by stirring overnight at room temperature. The HEC buffer was degassed under vacuum for 30 min, centrifuged for 20 min on a tabletop centrifuge, drawn into a 100-µl syringe, and 3 µl sample was used for injection into each capillary. Capillaries were prerun at 80 V/cm for 5 min before each experiment. Diluted and deionized PCR samples were injected by inserting the capillary in a 5-µl sample volume held in an Eppendorf tube followed by electrokinetic injection (80 V/cm for 3 s). After injection, the sample tubes were replaced with tubes containing 0.8% HEC plus ½×TBE buffer. Electrophoresis was performed at 80 V/cm using 5-capillary arrays held at ambient temperature (22° C.). The low (80 V/cm) electrophoresis voltage was used to avoid undersampling of the bands with our current detection system which is limited to 1 Hz scan rates. When the experiments were complete, capillaries were flushed with water, then with methanol followed by drying. These coated capillaries could be refilled 20–25 times before the quality of the separations deteriorated. Methods for the further extension of the lifetime of capillary columns have been described.

3. PCR Amplification of THO1 loci

DNA was isolated from blood by using standard methods (Puers et al. (1993) Am. J. Hum. Genet. 53, 953–958). The human tyrosine hydroxylase locus HUMTHO1, chromosomal location 11p15.5, contains a polymorphic four base STR sequence (AATG) in intron 1[Puers, 1993, 953]. PCR-amplification of this polymorphic region produces allelic fragments designated "5" through "11", according to the number of AATG repeats; an additional allele designated "9.3" differs from allele 10 by a single base deletion. The primer sequences used for PCR are 5'-ATTCAAAGGGTATCTGGGCTCTGG-3' (THO1-A) and 5'-GTGGGCTGAAAAGCTCCCGATTAT-3' (THO1-B) (Edwards et al. (1991) Am. J. Hum. Genet. 49, 746–756). PCR amplifications were performed in 50 µl volumes by using 10 ng genomic DNA template, 0.5 µM of each primer, 5 units Taq DNA polymerase, 50 mM KCl, 1.5 mM $MgCl_2$, 10 mM Tris-HCl at pH 8.3, and 200 µM dNTPs (final concentrations indicated). The PCR cycle protocol using a Perkin Elmer Cetus Model 480 was: (1) melting at 95° C. for 5 min, (2) 30 cycles of 95° C. for 1 min 58° C. for 1 min, and 72° C. for 1 min, (3) 72° C. for 7 min to complete extension. The PCR sample was then dialyzed for 30 min by pipeting 8–10 µl onto a 0.10 µm VCWP membrane filter (Millipore, Bedford, Mass.) which was floated on deionized water in a beaker held at 4° C. Dialysis was used to remove salts which can interfere with sample injection. Following dialysis, the samples were diluted with deionized water 100–1000 times (depending on product concentration) before electrokinetic injection. The amplifications with fluorescently labeled primers were also performed as described above. Initially four sets of fluorescent primers were used for PCR amplification and the mobility shifts of the products were evaluated with capillary electrophoresis. For these mobility shift experiments, 1–2 ng of unlabeled PCR product was reamplified by 20 PCR cycles using the appropriate fluorescent primers. THO1 types for all samples used in this study were independently determined by analysis on slab gels essentially as described by Puers et al., supra. Standard reference alleles were determined by sequence analysis.

4. Design and Synthesis of ET Primers

Chemicals were purchased from Applied Biosystems (Foster City, Calif.). Oligodeoxynucleotides were synthesized by the phosphoramidite method on an Applied Biosystems 392 DNA synthesizer. Absorption spectra of the primers were measured on a Perkin-Elmer Lambda 6 UV-visible spectrophotometer and fluorescence emission spectra were taken on a Perkin-Elmer model MPF 44B spectrofluorimeter.

The structures of the four ET primers and a representative synthetic reaction are presented in Scheme 2. The THO1 primer (24-bases long) with the sequence 5'-ATTCAAAGGGTATCTGGGCTCTGG-3' (THO1-A) and 5'-GTGGGCTGAAAAGCTCCCGATTAT-3' (THO1-B) were synthesized with donor-acceptor fluorophore pairs separated by different distances in the manner described above, where each of the 24-mers contains a modified base (T*) with the donor dye being attached to the 5' end of the oligomer, and the acceptor dye being attached to the primary amine group on the modified base (T*). As a representative example, the structure of F6R is shown below (Structure 3).

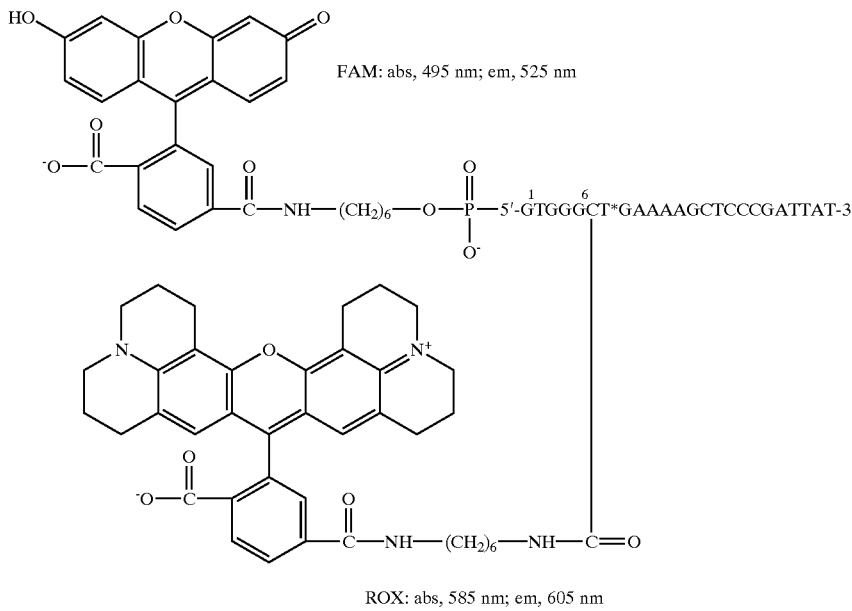

Structure 3. F6R

To prepare the ET primers, the donor FAM was introduced by using 6-FAM amidite in the last step of the oligonucleotide synthesis on a DNA synthesizer. After cleavage from the solid support and removal of the base protecting groups, the primers were evaporated to dryness under vacuum (0.5 mm Hg). To incorporate the acceptor dyes, 15–20 nmol of FAM-labeled T*-containing oligonucleotides in 40 µl 0.5 M $Na_2CO_3$/$NaHCO_3$ (pH 9.0) buffer were incubated overnight at room temperature with an approximately 150-fold excess of corresponding ROX or FAM N-hydroxy succinimidyl esters in 12 µl DMSO. Unreacted dye was removed by size exclusion chromatography on a Sephadex G-25 column (Pharmacia, Piscataway, N.J.). The ET primers were then purified by electrophoresis in a 20% polyacrylamide gel containing 6 M urea (40 cm×0.8 cm). The purified primers were recovered from the gel slices and desalted with Oligonucleotide Purification Cartridge (ABI). The single dye-labeled primers with the same sequence as that of the ET primers were prepared by the standard protocol using Aminolink 2 (ABI). The purity of the primers was shown to be >99% by polyacrylamide capillary gel electrophoresis. Primers were quantified by their 260 nm absorbances and then stored in 10 mM Tris-HCl, 1 mM EDTA (pH 8.0) at a final concentration of 10 pmol/µl for PCR reactions.

Figure 15:
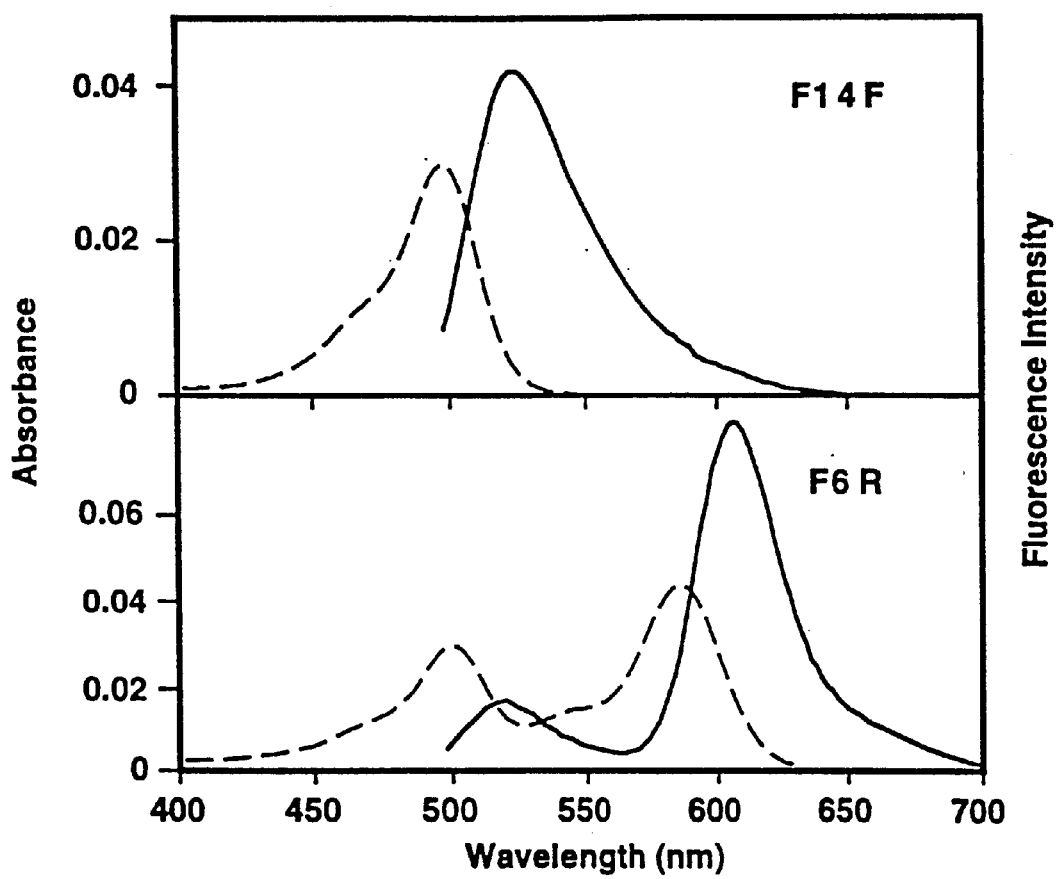
FIG. 15 shows the absorption (———) and fluorescence emission (———) spectra of the fluorescently labeled THO1 primers F14F and F6R measured in 1×TBE. F14F exhibits strong absorption at 488 nm and intense fluorescence emission with a maximum at 525 nm. F6R also exhibits intense absorption at 488 nm but the maximum emission is shifted out to 600 nm.
Figure 16:
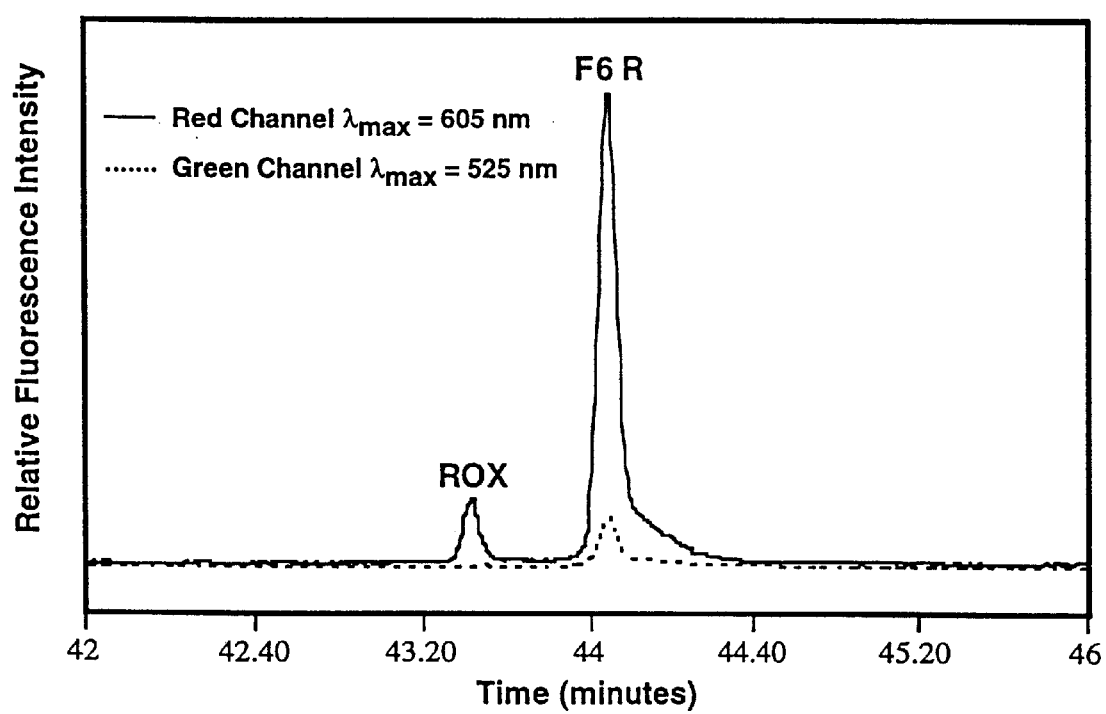
FIG. 16 shows the capillary electrophoresis (CE) electropherogram of primer F6R and ROX labeled primer. The two primers with the same sequence and same molar concentration were mixed together in 80% formamide and analyzed with a polyacrylamide gel filled capillary. The fluorescence signals were detected in the green (———) and red (———) channels simultaneously with 488 nm excitation (argon laser). The fluorescence signal intensity of F6R is 8-fold higher than that of ROX labeled primer.

Four ET primers (F2R, F6R, F10F and F14F) were synthesized with the same donor at 5' end and different acceptors at different positions on the primer sequence. The energy-transfer dye-labeled primers are advantageous for two-color fragment sizing because the 488-nm exciting light is optimally absorbed by the FAM chromophore in these primers followed by enhanced emission at the FAM wavelength in the case of F10F and F14F or very distinctively Stokes-shifted emission following energy transfer in the case of F2R and F6R. As representative examples, spectra of F14F and the energy transfer dye-labeled primer F6R are presented in FIG. 15. F14F exhibits strong absorption at ~488 nm and intense fluorescence emission with a maximum at 525 nm. F6R also exhibits intense absorption at 488 nm, but because of the FAM-to-ROX fluorescence energy transfer, the emission maximum is shifted out to ~600 nm and the energy transfer efficiency is over 90%. Substantial enhancement of the ET primer emission intensity compared to the single dye-labeled primer is observed. For example, FIG. 16 shows the fluorescence signal intensity comparison of the ET primer F6R with the corresponding single ROX-labeled primer in capillary electrophoresis. The two primers with the same sequence and same molar concentration were mixed together in 80% formamide and analyzed with a polyacrylamide gel filled capillary. The fluorescence intensity of F6R primer is 8-fold higher than and the ROX primer.

5. Evaluation of Energy Transfer Primer Labeling

For routine sizing experiments it is desirable to perform 2-color detection where the allelic standards are amplified with one fluorescent primer and the unknowns are amplified with a second fluorescent primer having a distinctive emission. Energy-transfer (ET) primers have the advantage of providing strong absorption at a common laser excitation wavelength (488 nm). Following the fluorescence energy transfer, the ET primers emit at a Stokes-shifted wavelength determined by the properties of the acceptor. Thus, the fluorescence emission of the ET primers is very intense, and the emission spectra of the different ET dye-labeled primers are distinctively Stokes-shifted. The ET primers can provide 8 times the signal strength compared to conventional single-dye labeled fluorescent primers as shown earlier. Furthermore, the mobility shift of DNA fragments generated with ET primers depends on the spacing between the dyes. Experiments were therefore performed to evaluate the mobility shift of the amplified fragments for all combinations of singly and doubly labeled targets.

Figure 17:
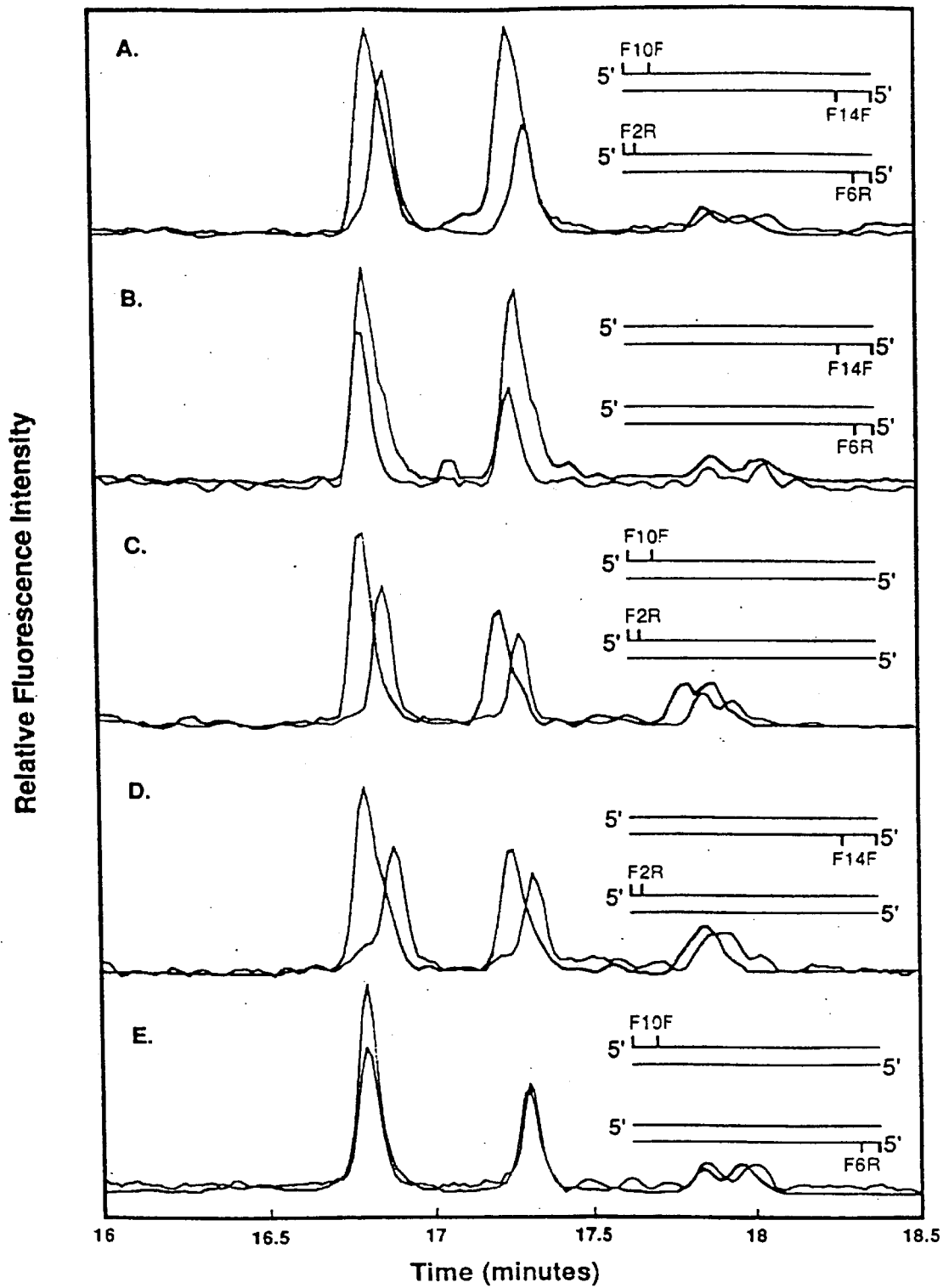
FIG. 17 shows the comparison of the mobility shift using five different ET primer-dependent methods for the amplification of the THO1 target alleles 6 and 9.3. The green line indicates the fluorescence intensity in the green channel and the red line indicates the intensity in the red channel. The structures of the primer sets used are indicated. Electrophoresis was performed using 0.8% HEC, ½×TBE and 1 $\mu$M 9-aminoacridine (9-AA) in the running buffer.

In trace A of FIG. 17, both strands of the amplified 6 and 9.3 targets have been labeled. In one case, the F10F primer is extended to form the (+) strand and the F14F primer is extended to form the (−) strand producing the green-emitting fragments. In the second case, the ET dye-labeled primer F2R is extended to produce the (+) strand and F6R is used to extend the (−) strand producing the red-emitting fragments. These fragments were mixed and electrophoresed on HEC-filled capillaries in the presence of 1 μM 9-aminoacridine (see below). The mobility shift between the green fragments and the red fragments in trace A was found to be ~2 bp. Thus, it was decided to evaluate amplifying with just one fluorescent primer per ds-DNA fragment to see if a particular combination of labels would reduce the mobility shift. Trace B in FIG. 17 shows that amplifying the (−) strand with the F14F primer or with the F6R primer generates fragments having almost no mobility shift (≦0.3 bp) between the green- and the red-labeled fragments. The two other labeling methods shown in traces C and D resulted in larger mobility shifts (2.4 bp). However, amplifying the (−) strand with F6R and the (+) strand with F10F also produced fragments having almost no mobility shift (trace E). The subsequent experiments were performed using the labeling method illustrated in trace B because these fragments are labeled on the same strand and can thus also be sized under denaturing conditions if necessary.

6. Resolution Enhancement with 9-Aminoacridine

To achieve satisfactory resolution of the THO1 allelic ladder, it was found that it is necessary to include an intercalating dye in the running buffer. Poorer resolution is obtained when the allelic ladder (amplified with the F6R primer) is run in 0.8% HEC alone. The separation of the same ladder in 0.8% HEC plus 1 μM of the intercalating dye thiazole orange (TO) provided dramatically enhanced resolution. Electrophoresis in the presence of the intercalator ethidium bromide has also been shown to improve the electrophoretic resolution of ds-DNA.(Schwartz et al. (1991) J. Chromatogr. 559, 267–283; Guttman et al. (1991) Anal. Chem. 63, 2038–2042). Unfortunately, TO contributes to the signal in the green channel of our two-color detection system rendering it unsuitable for use in the desired two-color labeling scheme. It is thus necessary to use a non-fluorescent intercalator to improve the resolution. In electrophoretic separations of preformed dimeric dye:DNA complexes, Zhu et al.((1994) Anal. Chem. 66, 1941–1948) observed that the addition of the non-fluorescent dye 9-aminoacridine (9-AA) can be used to dramatically improve ds-DNA separation much like TO and ethidium. Thus, the effect of 9-AA was evaluated. The separation is as good as that obtained in the presence of TO. The resolution improves significantly up to 1 μM 9-AA and is only slightly better at 5 μM. 9-AA concentrations above 50 μM were found to quench the fluorescence.

7. Two-color THO1 Sizing with Capillary Array Electrophoresis

Figure 18:
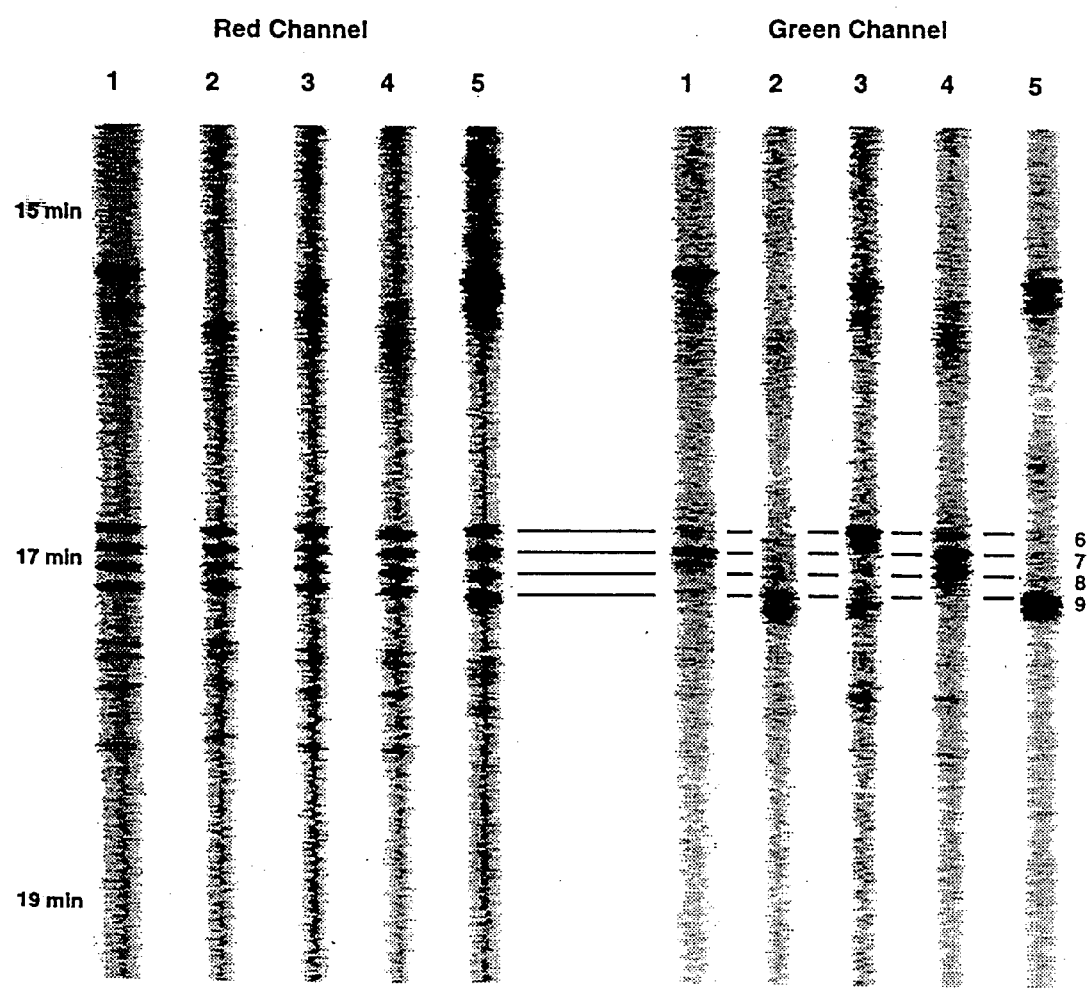
FIG. 18 shows the images of the fluorescence from a five capillary array separation of THO1 alleles. The left image presents the fluorescence signal as a function of time detected in the red (>590 nm) channel while the right image presents the fluorescence signal from the green ($\lambda$max=525 nm) channel. The standard THO1 allelic ladder (6+7+8+9) was amplified with the red emitting ET primer F6R and detected in the red channel; unknown alleles were amplified with the green emitting primer F14F and detected in the green channel. These images have been adjusted for the 1–2% capillary-to-capillary variance in mobility by shifting the time axes so that the allelic ladder is detected at the same time in all capillaries. This separation was performed with 0.8% HEC and 1 $\mu$M 9-AA in the running buffer at 80V/cm.
Figure 19:
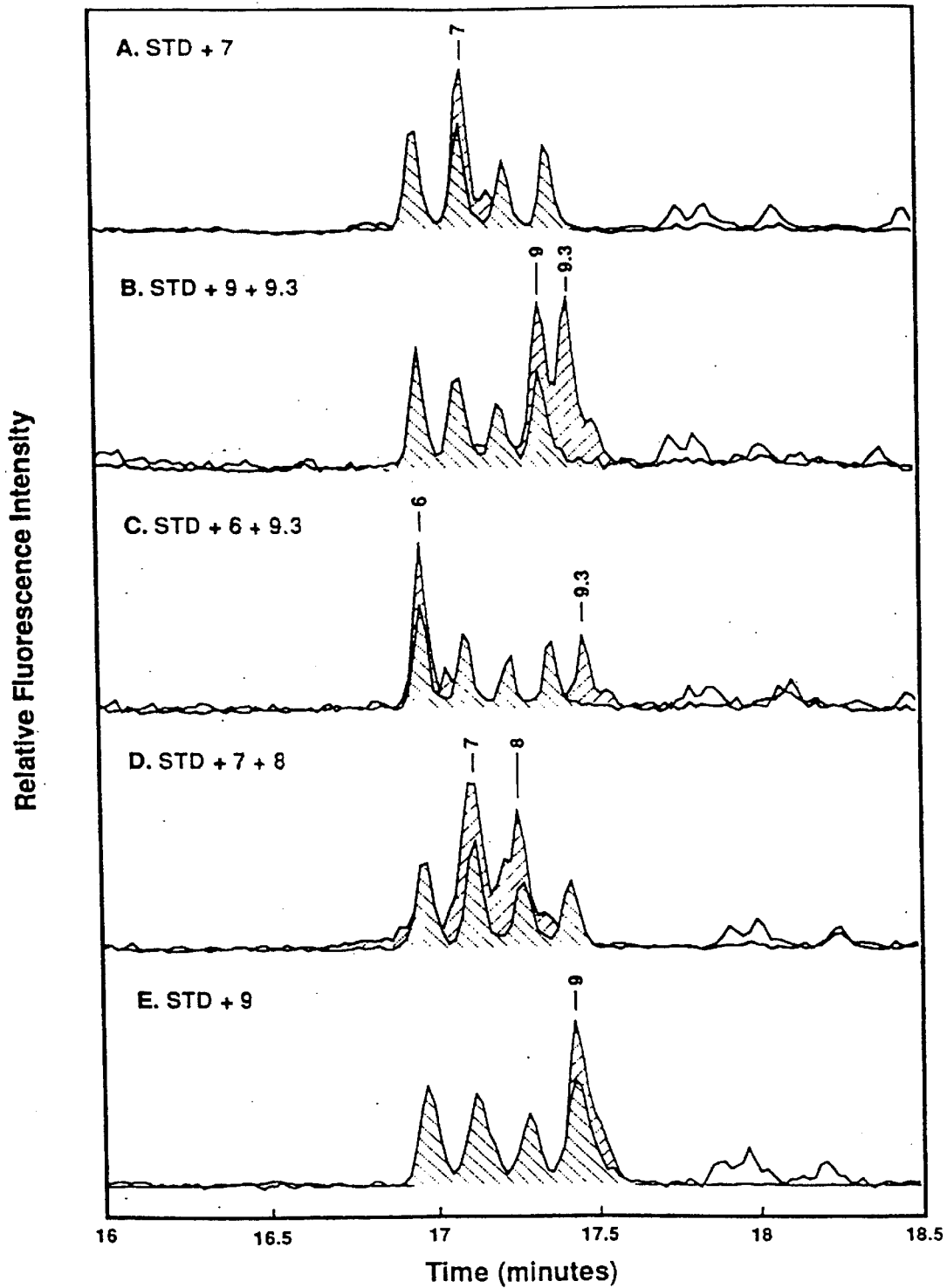
FIG. 19 shows the electropherograms of the THO1 fragment sizing separations presented in FIG. 18. The green signal is from the unknown alleles and the red signal is from the standard THO1 ladder. Traces A through E correspond to lanes 1–5 in FIG. 18.

FIG. 19 presents the results of a typical THO1 sizing experiment performed using two-color capillary array electrophoresis. The standard allelic ladder was amplified with F6R and detected in the red channel, while the unknown alleles were amplified with F14F and detected in the green channel. The signal detected as a function of time is presented as two images: the left image is the signal in the red channel and the right image is that detected in the green channel. The alleles appear at 17 minutes after injection. The signal in the red channel is predominantly from the red-labeled standard ladder and the expected 4 band patterns are seen in all capillaries. The unknown, amplified with the green emitting primer, is detected in the green channel. Allelic bands are identified as the intense green bands coinciding in mobility with allelic ladder bands in the red channel. To illustrate, the right image of FIG. 18 reveals intense green bands corresponding to allele 7 in lane 1, alleles 9+9.3 in lane 2, alleles 6+9.3 in lane 3, alleles 7+8 in lane 4, and allele 9 in lane 5. FIG. 19 presents electropherograms derived from the image in FIG. 18. Very clear discrimination is observed between the green-labeled fragments and the red-labeled fragments with almost no cross-talk between the green and red channels. In some cases, the amplification products of heterozygote samples contain heteroduplex bands that migrate behind the allelic ladder. Additional weak "noise" bands may represent non-templated base addition (Kimpton et al. (1993) PCR Methods and Applications 3, 13–22) known to occur with PCR amplification of THO1.

The accuracy and precision of allelic sizing using CAE was tested by performing multiple runs on 11 different samples. These results are summarized in Table 1.

TABLE 1

Statistical analysis of THO1 fragment sizing[1]

| Allele | Length (bp) | Determinations | Mean size[2] | S.D. (%)[3] |
| --- | --- | --- | --- | --- |
| 6   | 183 | 6  | 183.1 | 0.61 (0.33) |
| 7   | 187 | 23 | 187.0 | 0.41 (0.22) |
| 8   | 191 | 15 | 191.2 | 0.69 (0.36) |
| 9   | 195 | 11 | 195.4 | 0.60 (0.31) |
| 9.3 | 198 | 8  | 198.3 | 0.52 (0.26) |
| 10  | 199 | 6  | 199.0 | 0.31 (0.15) |

[1]Eleven different amplified samples (7, 8), (6, 9.3), (9, 9.3), (6, 9), (7, 8), (8, 9), (7, 9.3), (7, 10), 6, 9.3), (7) and (9) were run 8, 2, 4, 3, 5, 2, 1, 6, 1, 3 and 2 times, respectively.
[2]Mean PCR product size as determined by linear regression using the allelic ladder as the sizing standard.
[3]Standard Deviation in terms of base pairs for the indicated number of determinations. The percent relative S.D. is given in parentheses.

Since a linear relationship exists between molecular weight and migration time in the region of interest, the allelic ladder was used with a linear regression analysis to size the unknown fragments. The calculated sizes of unknown alleles are compared to true sizes based on sequence analysis and verified by denaturing polyacrylamide gel electrophoresis. The average absolute difference of the determined allele sizes from the true allele sizes was 0.41 and over 70% of the determined values were within 0.5 bp of the true value. The reproducibility is excellent (relative standard deviation less than 0.4% for each allele) and there was no ambiguity in allele assignments. Two alleles, 9.3 and 10, which differ by a single base pair deletion can not be electrophoretically resolved when paired but can be correctly assigned when in combination with any other allele. It should however be possible to separate these two fragments on columns containing higher concentrations of HEC.

8. Two-Color Sizing of Multiplexed STRs

Figure 20:
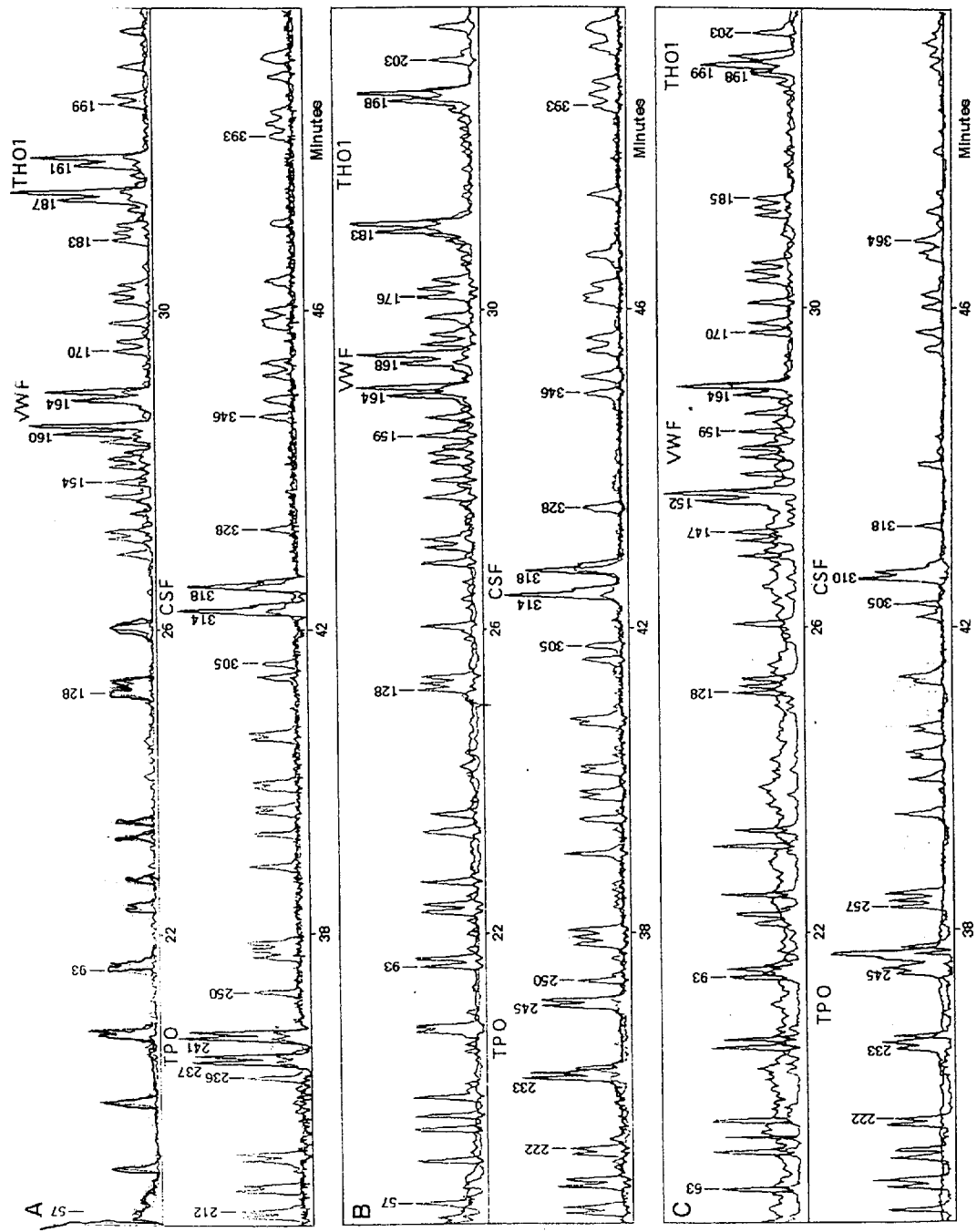
FIG. 20 shows representative electropherograms of three different multiplexed STR samples typed for VWFA, THO1, TPO and CSF loci (green). Each set of fragments is sized against an M13 A-termination standard generated with the F10R primer. Electrophoresis was performed with replaceable 2% HEC, 1×TBE, 6 M urea, 10% formamide sieving matrices at 200 V/cm. This figure has been processed with matrix transformation to correct for the spectral cross-talk between channels.

FIG. 20 presents three different capillary array electrophoresis separations of the VWFA, THO1, TPO and CSF STR tetraplex. Denaturing and replaceable HEC separation sieving matrices were used to achieve rapid (<50 min) separations. The VWFA, TPO and CSF loci were amplified with an F8F primer and the THO1 locus was amplified with an F6F primer. The data in FIG. 20 demonstrate that the four loci are evenly amplified. Since they are amplified with the F8F or F6F primers, they are only detected in the green channel. The cross-talk in the red M13 channel is low and can be easily removed by appropriate software filtering. Each locus is heterozygous except the CSF locus in trace C. In these runs, each allele is represented by doublet peaks; the first peak of each doublet is the desired PCR product and the second peak is a non-templated one-base addition.

In this study, we have investigated the use of an M13 sequencing ladder as a universal fragment sizing calibration standard; this standard is easily prepared from commercially available M13 templates. M13 A-, T-, C- and G-track ladders were individually prepared and tested singly and in paired combinations. The single track and pair track ladders were evaluated for evenness of peak distribution over the sizing range of interest (100–350 nucleotides), position of the landmark peaks to put the ladder into register, and linearity of the correlation of size to mobility. The M13 A-track was found to provide the best combination of peak spacing and linear correlation of size to mobility. Some compressions appeared in the C and G track ladders although the deviation from a linear correlation was small. The T-track had large gaps over the size range of interest. The M13 A-track was produced using an F10R labeled sequencing primer and was detected in the red channel.

Single base resolution is routinely achieved for the separation of M13 A-fragments up to 400 bp. The importance of single base resolution is illustrated in Trace C of FIG. 20 which shows the separation of the 9.3 and 10 alleles at the THO1 locus. Alleles 9.3 and 10, which differ by a single base deletion, produce a triplet peak in the electropherogram. The first peak is the desired 9.3 PCR product. The middle peak with high intensity is the overlap of the one-base addition to allele 10. For the THO1 locus the triplet structure is a nice indicator of the appearance of alleles 9.3 and 10. Lengthening the time of the final PCR extension reaction to 2 h or more results in near complete production of the non-templated base addition product, thus by-passing any interpretive ambiguity associated with this phenomenon. The extra peak in the high molecular weight allele of the TPO locus in Trace C is much stronger than the expected doublet peaks and this could be due to false PCR amplification.

It is evident from the above results, that one can tune related compositions, e.g. polynucleotides functionalized with 2 fluorophores to provide for different emission wavelengths and high emission quantum yields, while having substantially the same excitation-light absorbance and mobility. The subject labels can be readily prepared, can be used in a wide variety of contexts, and have good stability and enhanced fluorescent properties.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of identifying and distinguishing different deoxyribonucleic acids produced in chain termination sequencing reactions, said method comprising:

(a) producing a first, a second, a third, and a fourth set of different size deoxyribonucleic acids complementary to a deoxyribonucleic acid template using a nucleic acid polymerase, wherein:

said first set consists essentially of different size deoxyribonucleic acids covalently bonded to a first fluorescent energy-transfer label and terminates with a chain terminator comprising a nitrogenous base complementary to adenine, said second set consists essentially of different size deoxyribonucleic acids covalently bonded to a second fluorescent energy-transfer label and terminates with a chain terminator comprising a nitrogenous base complementary to guanine, said third set consists essentially of different size deoxyribonucleic acids covalently bonded to a third fluorescent energy-transfer label and terminates with a chain terminator comprising a nitrogenous base complementary to thymine, and said fourth set consists essentially of different size deoxyribonucleic acids covalently bonded to a fourth fluorescent energy-transfer label and terminates with a chain terminator comprising a nitrogenous base complementary to cytosine, provided that said first fluorescent energy-transfer label consists of a first specific chemical structure comprising a first fluorescent donor and a first fluorescent acceptor covalently bonded to a first backbone chain, with energy transfer from said first donor to said first acceptor, said second fluorescent energy-transfer label consists of a second specific chemical structure comprising a second fluorescent donor and a second fluorescent acceptor covalently bonded to a second backbone chain, with energy transfer from said second donor to said second acceptor, said third fluorescent energy-transfer label consists of a third specific chemical structure comprising a third fluorescent donor and a third fluorescent acceptor covalently bonded to a third backbone chain, with energy transfer from said third donor to said third acceptor, and said fourth fluorescent energy-transfer label consists of a fourth specific chemical structure comprising a fourth fluorescent donor and a fourth fluorescent acceptor covalently bonded to a fourth backbone chain, with energy transfer from said fourth donor to said fourth acceptor, further provided that the absorption wavelengths of said first donor, said second donor, said third donor, and said fourth donor are substantially the same and said first acceptor, said second acceptor, said third acceptor, and said fourth acceptor, each have different emission wavelengths;

(b) separating said different size deoxyribonucleic acids produced in said step (a); and (c) identifying and distinguishing said different size deoxyribonucleic acids complementary to said deoxyribonucleic acid template separated in said step (b) by irradiating with light absorbed by said first donor, said second donor, said third donor, and said fourth donor; and detecting light emission from said first acceptor, said second acceptor, said third acceptor, and said fourth acceptor.

2. A method of identifying and distinguishing different deoxyribonucleic acids produced in chain termination sequencing reactions, said method comprising:

(a) producing a first, a second, a third, and a fourth set of different size deoxyribonucleic acids complementary to a deoxyribonucleic acid template using a nucleic acid polymerase, wherein:

said first set consists of different size deoxyribonucleic acids covalently bonded to a first fluorescent energy-transfer label and terminates with a chain terminator comprising a nitrogenous base complementary to adenine, said second set consists essentially of different size deoxyribonucleic acids covalently bonded to a second fluorescent energy-transfer label and terminates with a chain terminator comprising a nitrogenous base complementary to guanine, said third set consists essentially of different size deoxyribonucleic acids covalently bonded to a third fluorescent energy-transfer label and terminates with a chain terminator comprising a nitrogenous base complementary to thymine, and said fourth set consists essentially of different size deoxyribonucleic acids covalently bonded to a fourth fluorescent energy-transfer label and terminates with a chain terminator comprising a nitrogenous base complementary to cytosine, provided that said first fluorescent energy-transfer label comprises a first fluorescent donor, a first fluorescent acceptor, and a first backbone chain, said second fluorescent energy-transfer label comprises a second fluorescent donor, a second fluorescent acceptor, and a second backbone chain, said third fluorescent energy-transfer label comprises a third fluorescent donor, a third fluorescent acceptor, and a third backbone chain, and said fourth fluorescent energy-transfer label comprises a fourth fluorescent donor, a fourth fluorescent acceptor, and a fourth backbone chain, provided further that said first donor and said first acceptor are covalently bonded to said first backbone chain to produce a first fluorescent energy-transfer label having essentially only one specific chemical structure with energy transfer from said first donor to said first acceptor, said second donor and said second acceptor are covalently bonded to said second backbone chain to produce a second fluorescent energy-transfer label having essentially only one specific chemical structure with energy transfer from said second donor to said second acceptor, said third donor and said third acceptor are covalently bonded to said third backbone chain to produce a third fluorescent energy-transfer label having essentially only one specific chemical structure with energy transfer from said third donor to said third acceptor, and said fourth donor and said fourth acceptor are covalently bonded to said fourth backbone chain to produce a fourth fluorescent energy-transfer label having essentially only one specific chemical structure with energy transfer from said fourth donor to said fourth acceptor, and further provided that the absorption wavelengths of said first donor, said second donor, said third donor, and said fourth donor are substantially the same and said first acceptor, said second acceptor, said third acceptor, and said fourth acceptor, each have different emission wavelengths;

(b) separating said different size deoxyribonucleic acids produced in said step (a); and (c) identifying and distinguishing the deoxyribonucleic acids separated in step (b) by irradiating with light absorbed by said first donor, said second donor, said third donor, and said fourth donor; and detecting light emission from said first acceptor, said second acceptor, said third acceptor, and said fourth acceptor.

3. A method of identifying and distinguishing different deoxyribonucleic acids produced in chain termination sequencing reactions, said method comprising:

(a) producing a first, a second, a third, and a fourth set of different size deoxyribonucleic acids complementary to a deoxyribonucleic acid template using a nucleic acid polymerase, wherein:

said first set consists essentially of different size deoxyribonucleic acids covalently bonded to a first fluorescent energy-transfer label and terminates with a chain terminator comprising a nitrogenous base complementary to adenine, said second set consists essentially of different size deoxyribonucleic acids covalently bonded to a second fluorescent energy-transfer label and terminates with a chain terminator comprising a nitrogenous base complementary to guanine, said third set consists essentially of different size deoxyribonucleic acids covalently bonded to a third fluorescent energy-transfer label and terminates with a chain terminator comprising a nitrogenous base complementary to thymine, and said fourth set consists essentially of different size deoxyribonucleic acids covalently bonded to a fourth fluorescent energy-transfer label and terminates with a chain terminator comprising a nitrogenous base complementary to cytosine, provided that said first fluorescent energy-transfer label is substantially pure and comprises a first fluorescent donor and a first fluorescent acceptor covalently bonded to a first backbone chain, with energy transfer from said first donor to said first acceptor, said second fluorescent energy-transfer label is substantially pure and comprises a second fluorescent donor and a second fluorescent acceptor covalently bonded to a second backbone chain, with energy transfer from said second donor to said second acceptor, said third fluorescent energy-transfer label is substantially pure and comprises a third fluorescent donor and a third fluorescent acceptor covalently bonded to a third backbone chain, with energy transfer from said third donor to said third acceptor, and said fourth fluorescent energy-transfer label is substantially pure and comprises a fourth fluorescent donor and a fourth fluorescent acceptor covalently bonded to a fourth backbone chain, with energy transfer from said fourth donor to said fourth acceptor, further provided that the absorption wavelengths of said first donor, said second donor, said third donor, and said fourth donor are substantially the same and said first acceptor, said second acceptor, said third acceptor, and said fourth acceptor, each have different emission wavelengths;

(b) separating said different size deoxyribonucleic acids complementary to said deoxyribonucleic acid template produced in said step (a); and (c) identifying and distinguishing said different size deoxyribonucleic acids complementary to said deoxyribonucleic acid template separated in said step (b) by irradiating with light absorbed by said first donor, said second donor, said third donor, and said fourth donor; and detecting light emission from said first acceptor, said second acceptor, said third acceptor, and said fourth acceptor.

4. A method of identifying and distinguishing different deoxyribonucleic acids produced in chain termination sequencing reactions, said method comprising:

(a) producing a first, a second, a third, and a fourth set of different size deoxyribonucleic acids complementary to a deoxyribonucleic acid template using a nucleic acid polymerase, wherein:

said first set consists essentially of different size deoxyribonucleic acids covalently bonded to a first fluorescent energy-transfer label and terminates with a chain terminator comprising a nitrogenous base complementary to adenine, said second set consists essentially of different size deoxyribonucleic acids covalently bonded to a second fluorescent energy-transfer label and terminates with a chain terminator comprising a nitrogenous base complementary to guanine, said third set consists essentially of different size deoxyribonucleic acids covalently bonded to a third fluorescent energy-transfer label and terminates with a chain terminator comprising a nitrogenous base complementary to thymine, and said fourth set consists essentially of different size deoxyribonucleic acids covalently bonded to a fourth fluorescent energy-transfer label and terminates with a chain terminator comprising a nitrogenous base complementary to cytosine, provided that said first fluorescent energy-transfer label comprises a first fluorescent donor, a first fluorescent acceptor, and a first backbone chain, said second fluorescent energy-transfer label comprises a second fluorescent donor, a second fluorescent acceptor, and a second backbone chain, said third fluorescent energy-transfer label comprises a third fluorescent donor, a third fluorescent acceptor, and a third backbone chain, and said fourth fluorescent energy-transfer label comprises a fourth fluorescent donor, a fourth fluorescent acceptor, and a fourth backbone chain, provided further that said first donor and said first acceptor are covalently bonded to said first backbone chain to produce a substantially pure first fluorescent energy-transfer label with energy transfer from said first donor to said first acceptor, said second donor and said second acceptor are covalently bonded to said second backbone chain to produce a substantially pure second fluorescent energy-transfer label with energy transfer from said second donor to said second acceptor, said third donor and said third acceptor are covalently bonded to said third backbone chain to produce a substantially pure third fluorescent energy-transfer label with energy transfer from said third donor to said third acceptor, and said fourth donor and said fourth acceptor are covalently bonded to said fourth backbone chain to produce a substantially pure fourth fluorescent energy-transfer label with energy transfer from said fourth donor to said fourth acceptor, and further provided that the absorption wavelengths of said first donor, said second donor, said third donor, and said fourth donor are substantially the same and said first acceptor, said second acceptor, said third acceptor, and said fourth acceptor, each have different emission wavelengths;

(b) separating said different size deoxyribonucleic acids produced in said step (a); and (c) identifying and distinguishing the deoxyribonucleic acids separated in step (b) by irradiating with light absorbed by said first donor, said second donor, said third donor, and said fourth donor; and detecting light emission from said first acceptor, said second acceptor, said third acceptor, and said fourth acceptor.

5. A method of identifying and distinguishing different deoxyribonucleic acids produced in chain termination sequencing reactions, said method comprising:

(a) producing a first, a second, a third, and a fourth set of different size deoxyribonucleic acids complementary to a deoxyribonucleic acid template using a nucleic acid polymerase, wherein:

said first set consists essentially of different size deoxyribonucleic acids covalently bonded to a first fluorescent energy-transfer label and terminates with a chain terminator comprising a nitrogenous base complementary to adenine, said second set consists essentially of different size deoxyribonucleic acids covalently bonded to a second fluorescent energy-transfer label and terminates with a chain terminator comprising a nitrogenous base complementary to guanine, said third set consists essentially of different size deoxyribonucleic acids covalently bonded to a third fluorescent energy-transfer label and terminates with a chain terminator comprising a nitrogenous base complementary to thymine, and said fourth set consists essentially of different size deoxyribonucleic acids covalently bonded to a fourth fluorescent energy-transfer label and terminates with a chain terminator comprising a nitrogenous base complementary to cytosine, provided that said first fluorescent energy-transfer label consists of a first specific chemical structure comprising a first fluorescent donor and a first fluorescent acceptor covalently bonded to a first covalently bonded chain of atoms, with energy transfer from said first donor to said first acceptor, said second fluorescent energy-transfer label consists of a second specific chemical structure comprising a second fluorescent donor and a second fluorescent acceptor covalently bonded to a second covalently bonded chain of atoms, with energy transfer from said second donor to said second acceptor, said third fluorescent energy-transfer label consists of a third specific chemical structure comprising a third fluorescent donor and a third fluorescent acceptor covalently bonded to a third covalently bonded chain of atoms, with energy transfer from said third donor to said third acceptor, and said fourth fluorescent energy-transfer label consists of a fourth specific chemical structure comprising a fourth fluorescent donor and a fourth fluorescent acceptor covalently bonded to a fourth covalently bonded chain of atoms, with energy transfer from said fourth donor to said fourth acceptor, further provided that the absorption wavelengths of said first donor, said second donor, said third donor, and said fourth donor are substantially the same and said first acceptor, said second acceptor, said third acceptor, and said fourth acceptor, each have different emission wavelengths;

(b) separating said different size deoxyribonucleic acids produced in said step (a); and (c) identifying and distinguishing said different size deoxyribonucleic acids complementary to said deoxyribonucleic acid template separated in said step (b) by irradiating with light absorbed by said first donor, said second donor, said third donor, and said fourth donor; and detecting light emission from said first acceptor, said second acceptor, said third acceptor, and said fourth acceptor.

6. A method of identifying and distinguishing different deoxyribonucleic acids produced in chain termination sequencing reactions, said method comprising:

(a) producing a first, a second, a third, and a fourth set of different size deoxyribonucleic acids complementary to a deoxyribonucleic acid template using a nucleic acid polymerase, wherein:

said first set consists essentially of different size deoxyribonucleic acids covalently bonded to a first fluorescent energy-transfer label and terminates with a chain terminator comprising a nitrogenous base complementary to adenine, said second set consists essentially of different size deoxyribonucleic acids covalently bonded to a second fluorescent energy-transfer label and terminates with a chain terminator comprising a nitrogenous base complementary to guanine, said third set consists essentially of different size deoxyribonucleic acids covalently bonded to a third fluorescent energy-transfer label and terminates with a chain terminator comprising a nitrogenous base complementary to thymine, and said fourth set consists essentially of different size deoxyribonucleic acids covalently bonded to a fourth fluorescent energy-transfer label and terminates with a chain terminator comprising a nitrogenous base complementary to cytosine, provided that said first fluorescent energy-transfer label comprises a first fluorescent donor, a first fluorescent acceptor, and a first covalently bonded chain of atoms, said second fluorescent energy-transfer label comprises a second fluorescent donor, a second fluorescent acceptor, and a second covalently bonded chain of atoms, said third fluorescent energy-transfer label comprises a third fluorescent donor, a third fluorescent acceptor, and a third covalently bonded chain of atoms, and said fourth fluorescent energy-transfer label comprises a fourth fluorescent donor, a fourth fluorescent acceptor, and a fourth covalently bonded chain of atoms, provided further that said first donor and said first acceptor are covalently bonded to said first covalently bonded chain of atoms to produce a first fluorescent energy-transfer label having essentially only one specific chemical structure with energy transfer from said first donor to said first acceptor, said second donor and said second acceptor are covalently bonded to said second covalently bonded chain of atoms to produce a second fluorescent energy-transfer label having essentially only one specific chemical structure with energy transfer from said second donor to said second acceptor, said third donor and said third acceptor are covalently bonded to said third covalently bonded chain of atoms to produce a third fluorescent energy-transfer label having essentially only one specific chemical structure with energy transfer from said third donor to said third acceptor, and said fourth donor and said fourth acceptor are covalently bonded to said fourth covalently bonded chain of atoms to produce a fourth fluorescent energy-transfer label having essentially only one specific chemical structure with energy transfer from said fourth donor to said fourth acceptor, and further provided that the absorption wavelengths of said first donor, said second donor, said third donor, and said fourth donor are substantially the same and said first acceptor, said second acceptor, said third acceptor, and said fourth acceptor, each have different emission wavelengths;

(b) separating said different size deoxyribonucleic acids produced in said step (a); and (c) identifying and distinguishing the deoxyribonucleic acids separated in step (b) by irradiating with light absorbed by said first donor, said second donor, said third donor, and said fourth donor; and detecting light emission from said first acceptor, said second acceptor, said third acceptor, and said fourth acceptor.

7. A method of identifying and distinguishing different deoxyribonucleic acids produced in chain termination sequencing reactions, said method comprising:

(a) producing a first, a second, a third, and a fourth set of different size deoxyribonucleic acids complementary to a deoxyribonucleic acid template using a nucleic acid polymerase, wherein:

said first set consists essentially of different size deoxyribonucleic acids covalently bonded to a first fluorescent energy-transfer label and terminates with a chain terminator comprising a nitrogenous base complementary to adenine, said second set consists essentially of different size deoxyribonucleic acids covalently bonded to a second fluorescent energy-transfer label and terminates with a chain terminator comprising a nitrogenous base complementary to guanine, said third set consists essentially of different size deoxyribonucleic acids covalently bonded to a third fluorescent energy-transfer label and terminates with a chain terminator comprising a nitrogenous base complementary to thymine, and said fourth set consists essentially of consists essentially of different size deoxyribonucleic acids covalently bonded to a fourth fluorescent energy-transfer label and terminates with a chain terminator comprising a nitrogenous base complementary to cytosine, provided that said first fluorescent energy-transfer label is substantially pure and comprises a first fluorescent donor and a first fluorescent acceptor covalently bonded to a first covalently bonded chain of atoms, with energy transfer from said first donor to said first acceptor, said second fluorescent energy-transfer label is substantially pure and comprises a second fluorescent donor and a second fluorescent acceptor covalently bonded to a second covalently bonded chain of atoms, with energy transfer from said second donor to said second acceptor, said third fluorescent energy-transfer label is substantially pure and comprises a third fluorescent donor and a third fluorescent acceptor covalently bonded to a third covalently bonded chain of atoms, with energy transfer from said third donor to said third acceptor, and said fourth fluorescent energy-transfer label is substantially pure and comprises a fourth fluorescent donor and a fourth fluorescent acceptor covalently bonded to a fourth covalently bonded chain of atoms, with energy transfer from said fourth donor to said fourth acceptor, further provided that the absorption wavelengths of said first donor, said second donor, said third donor, and said fourth donor are substantially the same and said first acceptor, said second acceptor, said third acceptor, and said fourth acceptor, each have different emission wavelengths;

(b) separating said different size deoxyribonucleic acids complementary to said deoxyribonucleic acid template produced in said step (a); and (c) identifying and distinguishing said different size deoxyribonucleic acids complementary to said deoxyribonucleic acid template separated in said step (b) by irradiating with light absorbed by said first donor, said second donor, said third donor, and said fourth donor; and detecting light emission from said first acceptor, said second acceptor, said third acceptor, and said fourth acceptor.

8. A method of identifying and distinguishing different deoxyribonucleic acids produced in chain termination sequencing reactions, said method comprising:

(a) producing a first, a second, a third, and a fourth set of different size deoxyribonucleic acids complementary to a deoxyribonucleic acid template using a nucleic acid polymerase, wherein:

said first set consists essentially of different size deoxyribonucleic acids covalently bonded to a first fluorescent energy-transfer label and terminates with a chain terminator comprising a nitrogenous base complementary to adenine, said second set consists essentially of different size deoxyribonucleic acids covalently bonded to a second fluorescent energy-transfer label and terminates with a chain terminator comprising a nitrogenous base complementary to guanine, said third set consists essentially of different size deoxyribonucleic acids covalently bonded to a third fluorescent energy-transfer label and terminates with a chain terminator comprising a nitrogenous base complementary to thymine, and said fourth set consists essentially of different size deoxyribonucleic acids covalently bonded to a fourth fluorescent energy-transfer label and terminates with a chain terminator comprising a nitrogenous base complementary to cytosine, provided that said first fluorescent energy-transfer label comprises a first fluorescent donor, a first fluorescent acceptor, and a first covalently bonded chain of atoms, said second fluorescent energy-transfer label comprises a second fluorescent donor, a second fluorescent acceptor, and a second covalently bonded chain of atoms, said third fluorescent energy-transfer label comprises a third fluorescent donor, a third fluorescent acceptor, and a third covalently bonded chain of atoms, and said fourth fluorescent energy-transfer label comprises a fourth fluorescent donor, a fourth fluorescent acceptor, and a fourth covalently bonded chain of atoms, provided further that said first donor and said first acceptor are covalently bonded to said first covalently bonded chain of atoms to produce a substantially pure first fluorescent energy-transfer label with energy transfer from said first donor to said first acceptor, said second donor and said second acceptor are covalently bonded to said second covalently bonded chain of atoms to produce a substantially pure second fluorescent energy-transfer label with energy transfer from said second donor to said second acceptor, said third donor and said third acceptor are covalently bonded to said third covalently bonded chain of atoms to produce a substantially pure third fluorescent energy-transfer label with energy transfer from said third donor to said third acceptor, and said fourth donor and said fourth acceptor are covalently bonded to said fourth covalently bonded chain of atoms to produce a substantially pure fourth fluorescent energy-transfer label with energy transfer from said fourth donor to said fourth acceptor, and further provided that the absorption wavelengths of said first donor, said second donor, said third donor, and said fourth donor are substantially the same and said first acceptor, said second acceptor, said third acceptor, and said fourth acceptor, each have different emission wavelengths;

(b) separating said different size deoxyribonucleic acids produced in said step (a); and (c) identifying and distinguishing the deoxyribonucleic acids separated in step (b) by irradiating with light absorbed by said first donor, said second donor, said third donor, and said fourth donor; and detecting light emission from said first acceptor, said second acceptor, said third acceptor, and said fourth acceptor.

9. The method of claim 1, 2, 3, or 4, wherein said first donor, said second donor, said third donor and said fourth donor are the same.

10. The method of claim 1, 2, 3, or 4 wherein said first backbone chain is derived from a first bi-functional structure, said second backbone chain is derived from a second bi-functional structure, said third backbone chain is derived from a third bi-functional structure, and said fourth backbone chain is derived from a fourth bi-functional structure.

11. The method of claim 5, 6, 7, or 8 wherein said first covalently bonded chain of atoms is derived from a first bi-functional structure, said second covalently bonded chain of atoms is derived from a second bi-functional structure, said third covalently bonded chain of atoms is derived from a third bi-functional structure, and said fourth covalently bonded chain of atoms is derived from a fourth bi-functional structure.

12. The method of claim 1, 2, 3, or 4 wherein said first backbone chain, said second backbone chain, said third backbone chain, and said fourth backbone chain are the same or different.

13. The method of claim 5, 6, 7, or 8 wherein said first covalently bonded chain of atoms, said second covalently bonded chain of atoms, said third covalently bonded chain of atoms, and said fourth covalently bonded chain of atoms are the same or different.

14. The method of claim 10, wherein said first bi-functional structure, said second bi-functional structure, said third bi-functional structure, and said fourth bi-functional structure are the same or different.

15. The method of claim 11, wherein said first bi-functional structure, said second bi-functional structure, said third bi-functional structure, and said fourth bi-functional structure are the same or different.

16. The method of claim 10, wherein said first bi-functional structure comprises two amine functional groups, said second bi-functional structure comprises two amine functional groups, said third bi-functional structure comprises two amine functional groups, and said fourth bi-functional structure comprises two amine functional groups.

17. The method of claim 11, wherein said first bi-functional structure comprises two amine functional groups, said second bi-functional structure comprises two amine functional groups, said third bi-functional structure comprises two amine functional groups, and said fourth bi-functional structure comprises two amine functional groups.

18. The method of claim 10, wherein said first bi-functional structure comprises a ring structure, said second bi-functional structure comprises a ring structure, said third bi-functional structure comprises a ring structure, and said fourth bi-functional structure comprises a ring structure.

19. The method of claim 11, wherein said first bi-functional structure comprises a ring structure, said second bi-functional structure comprises a ring structure, said third bi-functional structure comprises a ring structure, and said fourth bi-functional structure comprises a ring structure.

20. The method of claim 1, 2, 3, 4, 5, 6, 7, or 8, wherein said first fluorescent energy-transfer label is joined to said chain terminator comprising a nitrogenous base complementary to adenine, said second fluorescent energy-transfer label is joined to said second chain terminator comprising a nitrogenous base complementary to guanine, said third fluorescent energy-transfer label is joined to said third chain terminator comprising a nitrogenous base complementary to thymine, and said fourth fluorescent energy-transfer label is joined to said fourth chain terminator comprising a nitrogenous base complementary to cytosine.

21. The method of claim 20, wherein said first fluorescent energy-transfer label is joined by a first linking arm to said chain terminator comprising a nitrogenous base complementary to adenine and said second fluorescent energy-transfer label is joined by a second linking arm to said second chain terminator comprising a nitrogenous base complementary to guanine, said third fluorescent energy-transfer label is joined by a third linking arm to said third chain terminator comprising a nitrogenous base complementary to thymine, and said fourth fluorescent energy-transfer label is joined by a fourth linking arm to said fourth chain terminator comprising a nitrogenous base complementary to cytosine.

22. The method of claim 1, 2, 3, 4, 5, 6, 7 or 8 wherein a first linking arm, a second linking arm, a third linking arm, and a fourth linking arm are the same or different.

23. The method of claim 1, 2, 3, 4, 5, 6, 7, or 8, wherein said first label, said second label, said third label, and said fourth label each have substantially the same mobility under conditions used in said step (b).

24. The method of claim 1, 2, 3, 4, 5, 6, 7, or 8, wherein said first label, said second label, said third label, and said fourth label have a mobility different by not more than 10% under conditions used in said step (b).

25. The method of claim 1, 2, 3, 4, 5, 6, 7, or 8, wherein said first label, said second label, said third label, and said fourth label each have a mobility different by not more than 5% under conditions used in step (b).

26. The method of claim 1, 2, 3, 4, 5, 6, 7, or 8, wherein said first label, said second label, said third label, and said fourth label have the same mobility under conditions used in step (b).

27. The method of claim 1, 2, 3, 4, 5, 6, 7, or 8, wherein said first, second, third, and fourth set of different size nucleic acids complementary to a deoxyribonucleic acid template are produced as a mixture of sets of different size deoxyribonucleic acids.

28. The method of claim 1, 2, 3, 4, 5, 6, 7, or 8, wherein said first fluorescent energy transfer label is FAM-10-FAM and said second fluorescent energy transfer label is FAM-3-ROX.

29. The method of claim 1, 2, 3, 4, 5, 6, 7, or 8, wherein said first fluorescent energy transfer label is FAM-10-FAM, said second fluorescent energy transfer label is FAM-10-JOE, said third fluorescent energy transfer label is FAM-10-TAMRA, and said fourth fluorescent energy transfer label is FAM-10-ROX.

30. The method of claim 1, 2, 3, 4, 5, 6, 7, or 8, wherein said first fluorescent energy transfer label is FAM-10-FAM, said second fluorescent energy transfer label is FAM-10-JOE, said third fluorescent energy transfer label is FAM-3-TAMRA, and said fourth fluorescent energy transfer label is selected from the group consisting of FAM-3-ROX and FAM-10-ROX.

\* \* \* \* \*